United States Patent
Love et al.

(10) Patent No.: US 12,285,320 B2
(45) Date of Patent: Apr. 29, 2025

(54) SENSOR FOR ABSORBENT ARTICLE

(71) Applicant: Medline Industries, Inc., Northfield, IL (US)

(72) Inventors: Daniel Love, Libertyville, IL (US); David Noskowicz, Spring Grove, IL (US); Vladimir Anastasov, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 263 days.

(21) Appl. No.: 17/497,691

(22) Filed: Oct. 8, 2021

(65) Prior Publication Data
US 2022/0023108 A1    Jan. 27, 2022

Related U.S. Application Data

(63) Continuation of application No. 15/913,045, filed on Mar. 6, 2018, now Pat. No. 11,173,074.
(Continued)

(51) Int. Cl.
*A61F 13/42* (2006.01)
*A61F 13/0206* (2024.01)
(Continued)

(52) U.S. Cl.
CPC .......... *A61F 13/42* (2013.01); *A61F 13/0209* (2013.01); *A61F 13/53* (2013.01);
(Continued)

(58) Field of Classification Search
CPC .... A61F 13/42; A61F 13/44; A61F 2013/422; A61F 2013/423; A61F 2013/424
See application file for complete search history.

(56) References Cited

U.S. PATENT DOCUMENTS

| 4,834,733 A | 5/1989 | Huntoon et al. |
| 5,266,928 A | 11/1993 | Johnson |

(Continued)

FOREIGN PATENT DOCUMENTS

| WO | 02078513 A2 | 10/2002 |
| WO | 2002078513 A8 | 4/2003 |

(Continued)

OTHER PUBLICATIONS

Notification of Transmittal of the International Search Report and the Written Opinion of the International Searching Authority, or the Declaration; International Application No. PCT/US2017/038146; Medline Industries, LP (Christiansen); Oct. 30, 2017.

(Continued)

*Primary Examiner* — Catharine L Anderson
(74) *Attorney, Agent, or Firm* — SandBright, PLLC; Robert Dan Spendlove

(57) ABSTRACT

An absorbent structure, including a sensor system, can sense and measure the level of wetness contained within the absorbent structure as well as sense and measure environmental conditions. The sensor system may include passive RFID sensors or tags, RFID readers, antenna, a tuning module, a processing module, a memory module and a wireless communication module. The absorbent structure may further include two or more sensors, with a first sensor placed in a first area most likely to first be exposed to liquid and a second sensor spaced apart from the first sensor in an area likely to be exposed to liquid only after the absorbent structure has become more saturated.

20 Claims, 12 Drawing Sheets

Related U.S. Application Data

(60) Provisional application No. 62/503,487, filed on May 9, 2017, provisional application No. 62/468,009, filed on Mar. 7, 2017.

(51) Int. Cl.
| | |
|---|---|
| *A61F 13/53* | (2006.01) |
| *A61G 7/05* | (2006.01) |
| *G06K 7/10* | (2006.01) |
| *A61F 13/00* | (2006.01) |
| *A61F 13/51* | (2006.01) |
| *A61F 13/511* | (2006.01) |
| *A61H 9/00* | (2006.01) |
| *G01N 27/04* | (2006.01) |

(52) U.S. Cl.
CPC ........... *A61G 7/05* (2013.01); *G06K 7/10297* (2013.01); *A61F 13/00055* (2013.01); *A61F 2013/00944* (2013.01); *A61F 2013/424* (2013.01); *A61F 2013/51061* (2013.01); *A61F 2013/51066* (2013.01); *A61F 13/51104* (2013.01); *A61F 2013/530007* (2013.01); *A61F 2013/530481* (2013.01); *A61G 2203/30* (2013.01); *A61H 9/0092* (2013.01); *A61H 2201/164* (2013.01); *A61H 2201/165* (2013.01); *A61H 2201/1697* (2013.01); *A61H 2201/5058* (2013.01); *A61H 2201/5061* (2013.01); *A61H 2201/5071* (2013.01); *A61H 2201/5082* (2013.01); *A61H 2205/10* (2013.01); *G01N 27/048* (2013.01); *H04Q 2213/13095* (2013.01)

(56) References Cited

U.S. PATENT DOCUMENTS

| | | | |
|---|---|---|---|
| 5,291,181 | A | 3/1994 | Deponte |
| 5,443,082 | A | 8/1995 | Mewburn |
| 5,459,452 | A | 10/1995 | Deponte |
| 5,468,236 | A | 11/1995 | Everhart et al. |
| 5,469,145 | A | 11/1995 | Johnson |
| 5,570,082 | A | 10/1996 | Mahgerefteh et al. |
| 5,796,345 | A | 8/1998 | Leventis et al. |
| 5,838,240 | A | 11/1998 | Johnson |
| 5,868,723 | A | 2/1999 | Al-Sabah |
| 6,097,297 | A | 8/2000 | Fard |
| 6,203,496 | B1 | 3/2001 | Gael et al. |
| 6,373,395 | B1 | 4/2002 | Kimsey |
| 6,384,728 | B1 | 5/2002 | Kanor et al. |
| 6,464,635 | B1 | 10/2002 | Cerrato et al. |
| 6,559,772 | B2 | 5/2003 | Zand et al. |
| 6,583,722 | B2 | 6/2003 | Jeutter et al. |
| 6,603,403 | B2 | 8/2003 | Jeutter et al. |
| 6,617,488 | B1 | 9/2003 | Springer et al. |
| 6,756,521 | B1 | 6/2004 | Breitkopf |
| 6,774,800 | B2 | 8/2004 | Friedman et al. |
| 6,870,479 | B2 | 3/2005 | Gabriel |
| 6,970,091 | B2 | 11/2005 | Roe |
| 6,981,951 | B1 | 1/2006 | Rahe |
| 7,053,781 | B1 | 5/2006 | Haire et al. |
| 7,176,344 | B2 * | 2/2007 | Gustafson .............. A61F 13/42 340/573.5 |
| 7,295,125 | B2 | 11/2007 | Gabriel |
| 7,314,752 | B2 | 1/2008 | Kritzman et al. |
| 7,321,315 | B2 | 1/2008 | Brumm et al. |
| 7,352,286 | B2 | 4/2008 | Chan et al. |
| 7,355,090 | B2 | 4/2008 | Ales, III et al. |
| 7,394,391 | B2 | 7/2008 | Long |
| 7,477,156 | B2 | 1/2009 | Long et al. |
| 7,498,478 | B2 | 3/2009 | Long et al. |
| 7,541,177 | B2 | 6/2009 | Kritzman et al. |
| 7,642,396 | B2 | 1/2010 | Ales, III et al. |
| 7,649,125 | B2 | 1/2010 | Ales, III et al. |
| 7,699,823 | B2 | 4/2010 | Haggstrom et al. |
| 7,846,383 | B2 | 12/2010 | Song |
| 7,947,467 | B2 | 5/2011 | Kritzman et al. |
| 7,956,754 | B2 | 6/2011 | Long |
| 7,977,529 | B2 | 7/2011 | Bergman et al. |
| 8,032,426 | B2 | 10/2011 | Williams et al. |
| 8,043,272 | B2 | 10/2011 | Long et al. |
| 8,044,257 | B2 | 10/2011 | Song |
| 8,101,813 | B2 | 1/2012 | Ales et al. |
| 8,112,322 | B2 | 2/2012 | Williams et al. |
| 8,190,495 | B1 | 5/2012 | Williams et al. |
| 8,196,809 | B2 | 6/2012 | Thorstensson |
| 8,237,572 | B2 | 8/2012 | Clement et al. |
| 8,248,249 | B2 | 8/2012 | Clement et al. |
| 8,274,393 | B2 | 9/2012 | Ales et al. |
| 8,314,284 | B1 | 11/2012 | Novello |
| 8,376,232 | B2 | 2/2013 | Eckstein et al. |
| 8,378,167 | B2 | 2/2013 | Allen et al. |
| 8,421,636 | B2 | 4/2013 | Collette et al. |
| 8,471,715 | B2 | 6/2013 | Solazzo et al. |
| 8,552,250 | B2 | 10/2013 | Robles et al. |
| 8,604,268 | B2 | 12/2013 | Cohen et al. |
| 8,697,933 | B2 | 4/2014 | Ales, III et al. |
| 8,698,641 | B2 | 4/2014 | Abraham et al. |
| 8,866,624 | B2 | 10/2014 | Ales, III et al. |
| 8,871,994 | B2 | 10/2014 | Wei et al. |
| 8,884,769 | B2 | 11/2014 | Novak |
| 8,962,909 | B2 | 2/2015 | Groosman et al. |
| 8,978,452 | B2 | 3/2015 | Johnson et al. |
| 9,107,776 | B2 | 8/2015 | Bergman et al. |
| 9,132,044 | B2 | 9/2015 | Sjoholm et al. |
| 9,138,354 | B2 | 9/2015 | Nhan et al. |
| 9,160,054 | B2 | 10/2015 | Yu et al. |
| 9,194,833 | B2 | 11/2015 | Bosaeus et al. |
| 9,224,102 | B2 | 12/2015 | Barda et al. |
| 9,241,839 | B2 | 1/2016 | Abraham et al. |
| 9,278,033 | B2 | 3/2016 | Abraham et al. |
| 9,283,123 | B2 | 3/2016 | Lewis et al. |
| 9,291,589 | B2 * | 3/2016 | Wong .................. G01N 27/223 |
| 9,314,381 | B2 | 4/2016 | Curran et al. |
| 9,322,797 | B1 | 4/2016 | Lastinger et al. |
| 9,333,118 | B2 | 5/2016 | Elfstrom et al. |
| 9,366,644 | B1 | 6/2016 | Lastinger et al. |
| 9,582,981 | B2 | 2/2017 | Rokhsaz et al. |
| 9,646,073 | B2 | 5/2017 | Mashinchi et al. |
| 9,665,639 | B2 | 5/2017 | Mashin-Chi et al. |
| 9,713,554 | B2 | 7/2017 | Barda et al. |
| 9,895,272 | B2 | 2/2018 | Schmidt et al. |
| 9,913,608 | B2 | 3/2018 | Lewis et al. |
| 10,101,289 | B2 * | 10/2018 | Goenka .............. G01N 27/048 |
| 10,376,423 | B2 * | 8/2019 | Staton .................. A61B 5/7455 |
| 2004/0100376 | A1 | 5/2004 | Lye et al. |
| 2008/0054408 | A1 | 3/2008 | Tippey et al. |
| 2008/0274014 | A1 | 11/2008 | Jumonville et al. |
| 2008/0274495 | A1 | 11/2008 | Jumonville et al. |
| 2010/0089264 | A1 | 4/2010 | Warner |
| 2010/0168694 | A1 | 7/2010 | Gakhar et al. |
| 2011/0295619 | A1 | 12/2011 | Tough |
| 2012/0161960 | A1 | 6/2012 | Cheng et al. |
| 2012/0172825 | A1 | 7/2012 | Ales et al. |
| 2012/0173249 | A1 | 7/2012 | Popp et al. |
| 2013/0052432 | A1 | 2/2013 | Koebel et al. |
| 2013/0296739 | A1 | 11/2013 | Schultz |
| 2013/0345657 | A1 | 12/2013 | Nelson et al. |
| 2014/0063085 | A1 | 11/2014 | Warner et al. |
| 2014/0375297 | A1 | 12/2014 | Geiger et al. |
| 2015/0018792 | A1 | 1/2015 | Marsiquet et al. |
| 2015/0080819 | A1 | 3/2015 | Charna et al. |
| 2015/0199487 | A1 | 7/2015 | Grauds et al. |
| 2016/0166438 | A1 * | 6/2016 | Rovaniemi .............. A61B 5/00 493/320 |
| 2016/0267769 | A1 | 9/2016 | Rokhsaz et al. |
| 2016/0361209 | A1 | 12/2016 | Mashin-Chi et al. |
| 2017/0000655 | A1 | 1/2017 | Mashin-Chi et al. |

FOREIGN PATENT DOCUMENTS

| | | |
|---|---|---|
| WO | 2004021944 A1 | 3/2004 |
| WO | 2006058276 A2 | 6/2006 |

(56) References Cited

FOREIGN PATENT DOCUMENTS

| | | |
|---|---|---|
| WO | 2007125446 A1 | 11/2007 |
| WO | 2008130298 A1 | 10/2008 |
| WO | 2018165109 A1 | 9/2018 |

OTHER PUBLICATIONS

Notification of Transmittal of the International Search Report and the Written Opinion of the International Searching Authority, or the Declaration; International Application No. PCT/US2018/021070; Medline Industries, LP (Love); Jul. 5, 2018.

International Preliminary Report on Patentability; International Application No. PCT/US2018/021070; Medline Industries, LP (Love); Sep. 10, 2019.

Notification Concerning Transmittal of International Preliminary Report on Patentability; International Application No. PCT/US2018/021070; Medline Industries, LP (Love); Sep. 19, 2019.

\* cited by examiner

SENSOR FOR ABSORBENT ARTICLE

RELATED APPLICATIONS

This application is a continuation of commonly owned U.S. patent application Ser. No. 15/913,045, filed Mar. 6, 2018, which application claims the benefit of U.S. Provisional Patent Application Nos. 62/503,487, filed May 9, 2017, and 62/468,009, filed Mar. 7, 2017, each of which is incorporated herein by reference.

FIELD OF THE INVENTION

The present invention relates generally to absorbent articles and, in particular, to the use of wetness and other sensors.

BACKGROUND

Millions of people of all ages suffer from incontinence of the bowel or bladder. Whether an infant, adult, or elderly person, the underlying cause of incontinence varies but the method of treatment typically involves absorbent article products. Adult incontinent briefs, disposable diapers, pull-up diapers, protective underwear and underpads can alleviate some of the emotional and physical discomfort of incontinence by absorbing and containing liquid and other discharges from the human body to prevent body and clothing soiling.

Typical absorbent articles include a topsheet facing the wearer that permits fluid exudates to pass through and a backsheet that prevents the exudates from escaping from the absorbent article. Much advancement has been made in the art since the introduction of the disposable absorbent article, as shown, for example, in applicant's co-pending U.S. patent application Ser. No. 13/832,965, which is incorporated by reference herein. However, quality care for patients and other users of absorbent articles requires that the article be changed after being wetted, and most of these articles are not adapted to aid the caregiver in the monitoring of the status of the article.

In addition, other articles may be exposed to fluid exudates and require replacement, including absorbent pads, sheets, bedding, mattresses and various types of bandages.

For example, bed sores, also known as pressure ulcers or decubitus ulcers, are prevalent among people who are bed-ridden or otherwise immobilized. Skin ulcers can be caused by pressure exerted on the skin and soft tissues (e.g., the individual's body weight resting against a hard surface such as a bed or chair) and are exacerbated when the skin is also exposed to moisture (e.g., due to incontinence) and/or friction, heat, and shear forces, for example caused by moving or repositioning a bed-ridden patient.

Elderly nursing home residents are particularly vulnerable to pressure ulcers since they are frequently bed-ridden and incontinent. Approximately one out of ten nursing home residents have some form of pressure ulcers. Since pressure ulcers can be persistent and heal slowly, treating pressure ulcers once formed is thus expensive, so there is a significant need to minimize a patient's exposure to conditions that would cause such ulcers. Accordingly, there exists a need to monitor the condition of bedding, sheets and absorbent pads used with patients. There also exists a need to monitor the condition of anti-ulcer devices such as heel boots/protectors.

In a further example, mattresses used in care facilities may become contaminated with urine or other fluids that have penetrated through a sheet or cover. Current practice requires a caregiver or supplier to visually assess the mattress by removing the cover. Such assessment creates a risk of infection and cross-contamination. Accordingly, there exists a need, among others, to monitor mattresses without the need to remove covers and visually inspect the mattresses.

A number of devices and wetness detecting systems have been attempted to report when a diaper, bedding, or adult incontinence article becomes wet due to incontinence. For example, U.S. Pat. No. 8,421,636, which is incorporated herein by reference, describes a patient monitoring system that detects wetness in an absorbent article. However, such devices may be improved in various ways as set forth herein.

BRIEF DESCRIPTION OF THE DRAWINGS

Advantages of the invention will become apparent upon reading the following detailed description and upon reference to the drawings.

Figure 1:
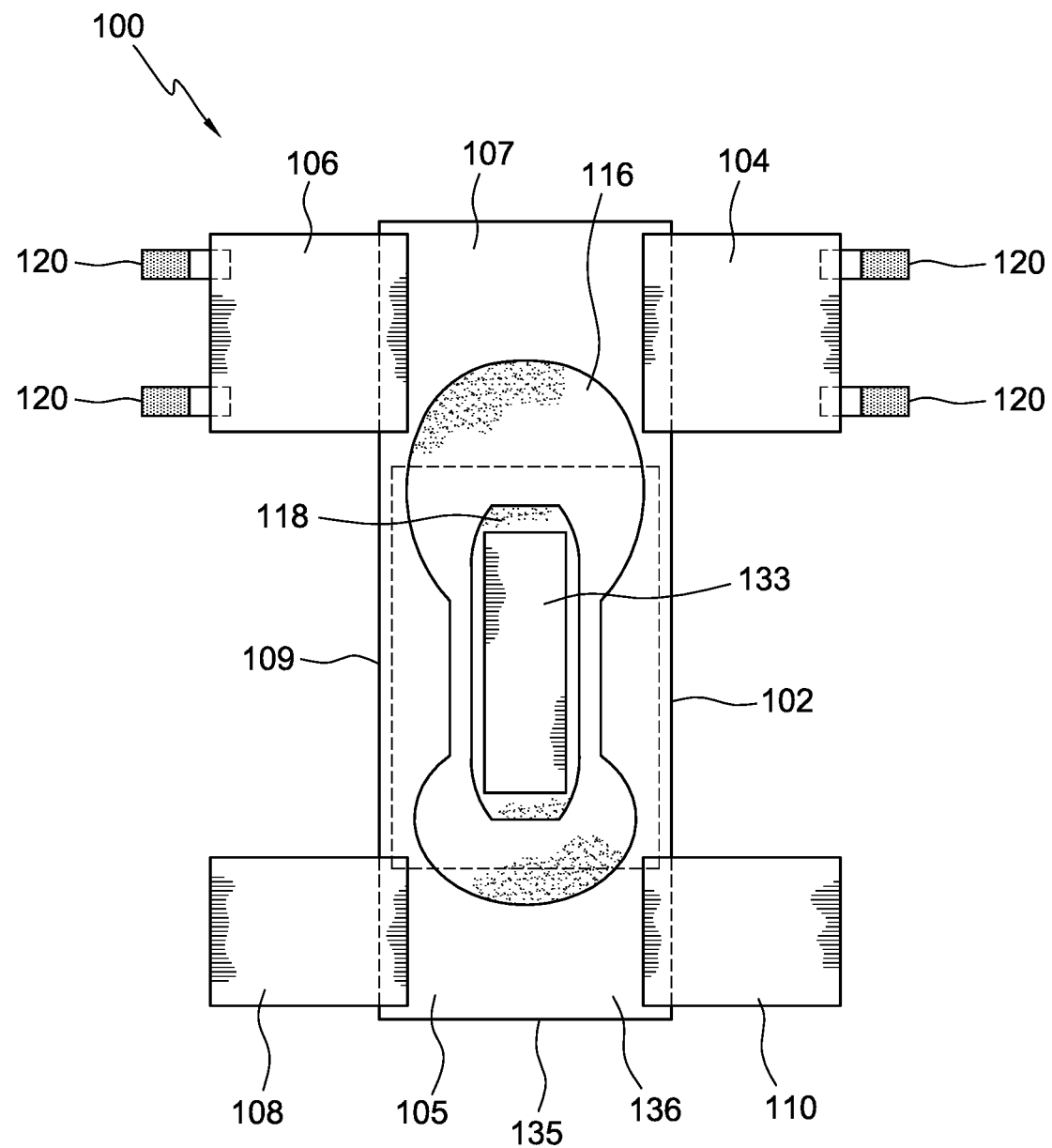
FIG. 1 is a top plan view of an absorbent article in a substantially flat un-contracted position according to one embodiment of the invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, and the like may be used solely to distinguish one entity or action from another entity or action without necessarily requiring or implying any actual such relationship, direction or order between such entities or actions.

Absorbent articles as described herein generally include a moisture-pervious inner layer, an absorbent layer, and a moisture-impervious outer layer. Although portions of the description will be specifically directed to adult incontinence articles, such as disposable diapers, it is to be understood that the embodiments may also be implemented using other absorbent articles and that the properties and uses described below apply to these other absorbent articles as well. Throughout this application, the terms absorbent article and diaper are used interchangeably. However, it should be understood that the term diaper is intended to include other absorbent articles, such as training pants, incontinence pads, etc., as would be understood by one of ordinary skill in the art. It should be further understood that the term absorbent article may refer to other absorbent structures used to absorb fluid associated with the care of patients. Such absorbent structures may include feminine hygienic pads, absorbent pads, mattresses, absorbent sheets, wound dressings and other absorbent structures. The terms user and patient are also used interchangeably to indicate a person in conjunction with whom the absorbent structure is used.

Figure 2:
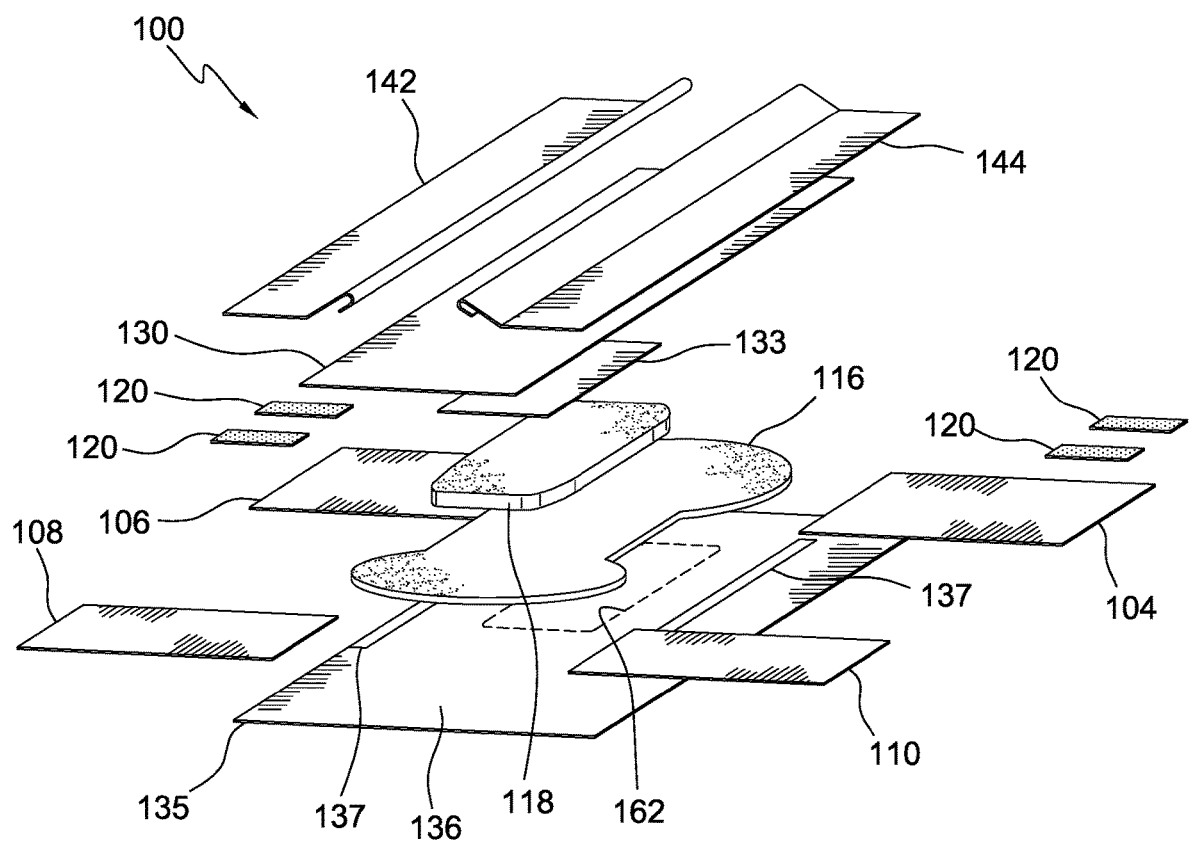
FIG. 2 is an exploded perspective view of the absorbent article of FIG. 1, again in a substantially flat un-contracted position.

FIGS. 1 and 2 illustrate an exemplary non-limiting general embodiment of an absorbent article 100. FIG. 1 illustrates a plan view of the absorbent article 100 in a substantially flat un-contracted state. As shown in these figures, the absorbent article 100 generally consists of several layers, including an inner layer, an absorbent layer, and an outer layer. The inner layer faces a wearer and contacts the skin of the wearer when the absorbent article 100 is secured to the wearer. The inner layer may comprise a topsheet 130 that is composed of a moisture-pervious fabric suitable to allow bodily discharge to pass through the inner layer and be absorbed by the absorbent layer. Non-limiting examples of materials suitable to form the topsheet 130 include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

The plan view of FIG. 1 is shown from the top or patient contacting side of the absorbent article. The topsheet (130) and other components have been removed for clarity. FIG. 2 is an exploded perspective view of the absorbent article 100. Again, the article 100 is shown in a substantially flat un-contracted state with certain items removed for clarity.

As shown in FIG. 1, an embodiment of the absorbent article 100 comprises a chassis 102. The chassis 102 includes a front waist region 105, a back waist region 107, and a crotch region 109 that is disposed longitudinally between the front and back waist regions 105 and 107. The front waist region 105 and the back waist region 107 generally comprise those portions of the absorbent article 100 which, when worn, encircle the waist of the wearer. The crotch region 109 is that portion of the absorbent article 100 which, when the absorbent article 100 is worn, is generally positioned between the legs of the wearer.

The chassis 102 has a shape such that its outer perimeter is rectangular or at least substantially rectangular in the illustrative embodiment of the absorbent article 100. In other embodiment, there may be portions of the chassis that are shaped and/or removed, such as in the crotch region 109, for example, resulting in a narrower crotch region portion 109 to provide a contoured fit between the legs. Still other embodiments have different shaped chassis, such as hourglass shapes, T-shapes, and the like.

Rear side panels 104, 106 are coupled to and may extend from the back waist region 105. The disposable article may further include front side panels 108, 110 that are coupled to and may extend from the front waist region 105. The back region 107 is generally positioned against the back of the user. The front region 105 is generally positioned against the front of the user. The rear side panels 104, 106 are configured to wrap around a wearer's waist from back to front, extending from each side of the back waist region 105. The front side panels 108, 110 are configured to wrap around a wearer's waist from front to back. In this manner, rear side panel 106 can be connected to front side panel 108 and rear side panel 104 can be connected to front side panel 110 to couple the front region 105 to the back region 107. In this embodiment there are four side panels 104, 106, 108, 110. However, it should be recognized that other embodiments may be configured with more or fewer side panels. In particular, rear side panels 104, 106 may connect directly to an outside surface of front waist region 105 rather than to front side panels 108, 110.

The side panels may attach to the chassis 102 in a variety of manners as would be apparent to one of skill in the art. For example, as described in applicant's co-pending U.S. patent application Ser. No. 13/832,965. Alternatively, one or more of the side panels may be integrally formed, in whole or in part, with a backsheet 135 or topsheet 130 of the absorbent article. The backsheet 135 will have an outside surface 134 facing away from the patient wearing the absorbent article and an inside surface 136 facing toward the patient.

The rear side panels 104, 106 may also include fasteners 120. Fasteners 120 may comprise adhesive tape, hook and loop, snaps or any other appropriate fasteners as would be understood by one of ordinary skill in the art. As shown in the illustrative embodiment, rear side panel 104, 106 includes two fasteners 120. In a preferred embodiment, fasteners 120 can be configured to operatively couple rear side panels 104, 106 to a front region 105 of the diaper chassis 102. Alternative, fasteners 120 may also engage front side panels 108, 110 to attach rear side panels 104, 106, respectively. While FIG. 1 depicts rear side panels 104, 106 as including two fasteners 120, in some embodiments, more or fewer fasteners may be used. While FIG. 1 depicts fasteners 120 sized and shaped a particular way, in other embodiments, fasteners 120 can be a different size and/or shape. Alternatively, the front side panels 108, 110 may include fasteners in additions to, or in place of, the fasteners 120 attached to rear side panels 104, 106.

In another embodiment, the front region 105 and/or front panels 108, 110 may include added or modified features to reinforce or increase the affinity to the fastening device. Additionally, features may be employed to allow adhesive fasteners to be attached and detached from the fastening region multiple times. Those skilled in the art will recognize that there are multiple approaches to doing so via modification of the base material as well as additions of various materials. For example, fasteners 120 may incorporate the hook component of a hook-and-loop closure and portions of the front region 105 and/or front panels 108, 110 may be comprise a corresponding loop component. The surface of front region 105 and/or front panels 108, 110 may be treated to increase or decrease the affinity for the hook components. Alternatively, separate loop component material may be adhered to the surface of the front region 105 and/or front panels 108, 110.

Referring again FIGS. 1 and 2, embodiments of the absorbent article 100 include an absorbent layer. The absorbent layer may comprise an acquisition and/or distribution ("A/D") layer 133, a first absorbent core 116, and a second absorbent core 118.

The liquid acquisition and/or distribution layers serves to rapidly acquire and then distribute acquired liquid to an absorbent core for retention. To achieve rapid acquisition and distribution, these layers often include cellulosic fibers. These layers can include cross-linked cellulosic fibers to impart bulk and resilience to the layer, and wood pulp fibers to increase the wicking of liquid within the layer and to facilitate distribution of the liquid throughout the layer and ultimately to another layer, such as a storage layer, that is in liquid communication with the distribution layer.

Figure 3:
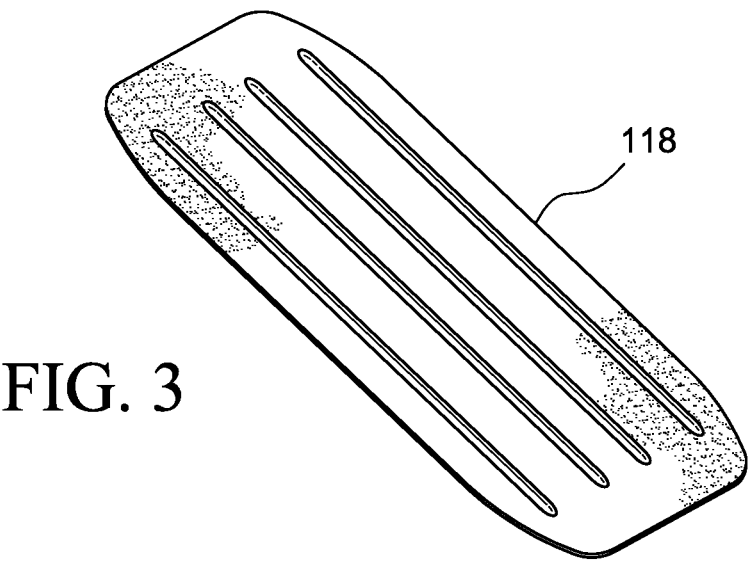
FIG. 3 is a perspective view of a second absorbent core of the absorbent article depicted in FIG. 1.
Figure 4:
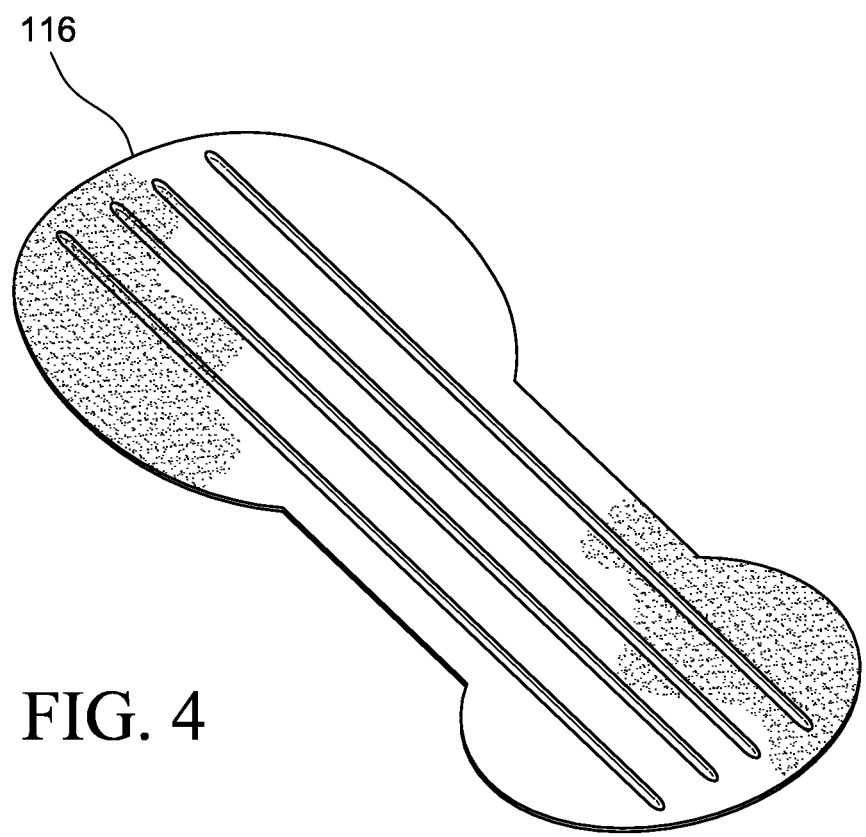
FIG. 4 is a perspective view of a first absorbent core of the absorbent article depicted in FIG. 1.

FIG. 3 is a perspective view of a top (facing towards wearer) of the second core 118, and FIG. 4 is a perspective view of a bottom side (facing away from a wearer) of the first core 116. Each of the first core 116 and second core 118 can be composed of similar material, and can be shaped depending on the size of the absorbent article, and whether it is intended for use by infants, children and/or adults. By way of example, and as shown in FIGS. 3 and 4, first core 116 can be larger and substantially hourglass shaped, whereas second core 118 can be smaller, relative to first core 116, and can be substantially rectangular shaped. In this manner, the absorbent article can include a large surface area of coverage provided by the first core 116, and the increased absorbency provided by the second core 118, without the additional bulk of a second core having the same size as the first core.

First core 116 is shown having an embossed bottom and second core 118 is shown having an embossed top. The embossed top of second core 118 and the embossed bottom of first core 116 provide increased longitudinal flow while reducing lateral flow, and, in this manner, reducing leakage. Said another way, the embossed top of second core 118 and the embossed bottom of first core 116 allows fluid to move longitudinally towards the front and the back of a wearer, as opposed to towards the legs of a wearer.

Each of the first core 116 and the second core 118 may be composed of any materials suitable for absorbing the fluids and discharge including, but not limited to, a fibrous material (e.g., fluffed wood pulp), a super absorbent polymer ("SAP"), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper may vary depending upon whether it is intended for use by infants, children and/or adults.

While FIGS. 3 and 4 depict the first core 116 having an embossed bottom, and the second core 118 having an embossed top, in some embodiments, an absorbent article can have only a single core with no embossing, a single core with embossing on both, and/or other combinations of one or two cores each with embossing on one, both, or neither side. While the figures show absorbent articles include one or two cores, in some embodiments, absorbent articles can include more or fewer cores.

FIGS. 3 and 4 depict embossing as including four spaced apart embossing "lines," in some embodiments. However, a core can include more or fewer embossing lines. In some embodiments, embossing lines can be adjacent one another, or can be a combination of adjacent and space apart embossing line. In this manner, the different combinations of embossing lines can define an embossing pattern. While FIGS. 3 and 4 depict embossing substantially along the entire width and length of each respective core, in some embodiments a core can have embossing substantially along an entire width and/or length, and/or a portion of a width and/or length.

In embodiments of the invention, the first 116 and second 118 cores may be created with or without the use of super absorbent polymer (SAP). While some literature indicates that the presence of SAP in a diaper used for urine testing is considered benign, manufacturing diapers without SAP for the benefit of accuracy is contemplated by the present invention and may be considered beneficial.

Returning to FIGS. 1 and 2, the absorbent article 100 may further include a set of leak guards and/or a set leg cuffs 142, 144, both known to those of ordinary skill in the art. Additionally, the exemplary absorbent article includes an outer layer or backsheet 135 and elastic bands 137. The elastic bands 137 can by used to gather the leg of the article around the user's leg, improving the fit of the absorbent article 100 and can improve the comfort of the wearer. Elastic bands and other elastic materials may be used at other places in the absorbent article in order to improve the fit and/or fluid retention of the article.

In further embodiments of the invention, the absorbent article includes a sensor system. The sensor system may function to sense a level of wetness and provide a means of measuring that wetness. Embodiments of the invention may include a passive radio frequency identification wetness sensor/tag as disclosed, for example, in U.S. Patent Application Publication No. 2016/0267769 (Sep. 15, 2016), which is incorporated herein by reference. As used herein, references to RFID tags or sensors may comprise, but are not limited to, such passive RFID sensors/tags.

These passive RFID moisture sensors may include an antenna coupled to a tail, a processing module, and a wireless communication module. The antenna and coupled tail have an impedance that may vary with an environment in which the antenna/tail is placed. The processing module couples to the antenna and has one or more self-tuning module(s) that may vary a reactive component impedance coupled to the antenna in order to change a system impedance. The system impedance may include the antenna impedance, tail impedance and the reactive component impedance. A self-tuning module(s) then produces an impedance value representative of the reactive component impedance. A memory module may store the impedance value which may then later is communicated to an RFID reader. The RFID reader then exchanges the impedance value representative of the reactive components of impedance with the RFID reader such that the RFID reader or another external processing unit or display device may process the impedance value in order to determine environmental conditions at the antenna. These environmental conditions may include but are not limited to temperature, humidity, wetness, or proximity of the RFID reader to the passive RFID sensor.

Additional sensors include battery-free RFID sensor chips that measure pressure and temperature. Such sensors may be readily embedded into the structure of absorbent articles, mattresses, wound dressings or the like. An example of such a sensor may use low frequency and magnetic radio coupling allows it to read through many materials. Examples of such sensors may include, without limitation, low frequency RFID passive wireless sensors offered by Phase IV Engineering Inc.

As discussed, wetness of an absorbent article such as a diaper may be an environmental condition that affects the impedance value. However, the position of the tag in relation to an insult to the absorbent article may affect the change in impedance and, therefore, the value reported by the tag when it is queried by the reader. Accordingly, embodiments of the present invention identify a proper placement of the tag depending upon the size of the absorbent article and whether the patient is male or female.

For example, in testing conducted by the applicant, two different briefs were tested. A small size of a first brief (FITULTRASM) was tested, and an extra-large size of a second brief (FITPLUSXLG) was tested. Eighteen specimens were tested—three specimens at each of three different positions were tested for each brief type. Specimens were tested using the female anatomy and lying in the supine position. A 250 mL insult of saline solution and a flow rate of 15 mL/sec were used. The brief was applied to the mannequin and an RFID tag was applied vertically to back outer layer of the brief, at different positions from the point of insult. Baseline readings of the tags were recorded. The insult was then delivered at a constant rate. Final readings of the tags were recorded. A summary of the findings is set forth below:

1. FITULTRASM 75 mm

Average Reading Change: 8.8±7.0

114 mm

Average Reading Change: 4.5±6.7

152 mm

Average Reading Change: 1.6±2.8

Refer to data tables on page 3.

2. FITPLUSXLG 100 mm

Average Reading Change: 7.5±1.2

152 mm

Average Reading Change: 4.2±5.4

200 mm

Average Reading Change: 3.8±1.2

Specific results for each test are provided in the following tables:

| Mannequin RFID Testing | | | |
|---|---|---|---|
| Material(s) | FITULTRASM | Date: | Mar. 28, 2017 |
| Test Conditions: | 22° C./33% RH | Volume Delivered: | 75 mL |
| Sample Conditioning: | N/A | Notes: | N/A |
| Position | Supine 75 mm from Point of Insult | | |
| Flow Rate | 15 mL/sec | | |
| | Baseline Reading | Final Reading | Delta |
| Specimen-1 | 14.4 | 26.0 | 11.6 |
| Specimen-2 | 15.2 | 16.0 | 0.8 |
| Specimen-3 | 14.7 | 28.6 | 13.9 |
| Mean: | 14.8 | 23.5 | 8.8 |
| Std Dev: | 0.4 | 6.7 | 7.0 |

| Mannequin RFID Testing | | | |
|---|---|---|---|
| Material(s) | FITPULTRASM | Date: | Mar. 28, 2017 |
| Test Conditions: | 22° C./33% RH | Volume Delivered: | 250 mL |
| Sample Conditioning: | N/A | Notes: | N/A |
| Position | Supine 114 mm from Point of Insult | | |
| Flow Rate | 15 mL/sec | | |
| | Baseline Reading | Final Reading | Delta |
| Specimen-1 | 15.4 | 16.2 | 0.8 |
| Specimen-2 | 14.0 | 14.4 | 0.4 |
| Specimen-3 | 15.4 | 27.6 | 12.2 |
| Mean: | 14.9 | 19.4 | 4.5 |
| Std Dev: | 0.8 | 7.2 | 6.7 |

| Mannequin RFID Testing | | | |
|---|---|---|---|
| Material(s) | FITULTRASM | Date: | Mar. 28, 2017 |
| Test Conditions: | 22° C./33% RH | Volume Delivered: | 250 mL |
| Sample Conditioning: | N/A | Notes: | N/A |
| Position | Supine 152 mm from Point of Insult | | |
| Flow Rate | 15 mL/sec | | |
| | Baseline Reading | Final Reading | Delta |
| Specimen-1 | 15.3 | 20.1 | 4.8 |
| Specimen-2 | 14.4 | 14.4 | 0.0 |
| Specimen-3 | 15.4 | 15.4 | 0.0 |
| Mean: | 15.0 | 16.6 | 1.6 |
| Std Dev: | 0.6 | 3.0 | 2.8 |

| Mannequin RFID Testing | | | |
|---|---|---|---|
| Material(s) | FITPLUSXLG | Date: | Mar. 28, 2017 |
| Test Conditions: | 22° C./33% RH | Volume Delivered: | 250 mL |
| Sample Conditioning: | N/A | Notes: | N/A |
| Position | Supine 100 mm from Point of Insult | | |
| Flow Rate | 15 mL/sec | | |
| | Baseline Reading | Final Reading | Delta |
| Specimen-1 | 14.9 | 23.3 | 8.4 |
| Specimen-2 | 14.6 | 20.8 | 6.2 |
| Specimen-3 | 15.8 | 23.7 | 7.9 |
| Mean: | 15.1 | 22.6 | 7.5 |
| Std Dev: | 0.6 | 1.6 | 1.2 |

| Mannequin RFID Testing | | | |
|---|---|---|---|
| Material(s) | FITPLUSXLG | Date: | Mar. 6, 2017 |
| Test Conditions: | 22° C./40% RH | Volume Delivered: | 250 mL |

-continued

Mannequin RFID Testing

| Sample Conditioning: | N/A | Notes: | N/A |
|---|---|---|---|
| Position | Supine 152 mm from Point of Insult | | |
| Flow Rate | 15 mL/sec | | |
| | Baseline Reading | Final Reading | Delta |
| Specimen-1 | 15.6 | 16.0 | 0.4 |
| Specimen-2 | 15.4 | 17.3 | 1.9 |
| Specimen-3 | 15.6 | 26.0 | 10.4 |
| Mean: | 15.5 | 19.8 | 4.2 |
| Std Dev: | 0.1 | 5.4 | 5.4 |

Mannequin RFID Testing

| Material(s) | FITPLUSXLG | Date: | Mar. 6, 2017 |
|---|---|---|---|
| Test Conditions: | 22° C./40% RH | Volume Delivered: | 250 mL |
| Sample Conditioning: | N/A | Notes: | N/A |
| Position | Supine 200 mm from Point of Insult | | |
| Flow Rate | 15 mL/sec | | |
| | Baseline Reading | Final Reading | Delta |
| Specimen-1 | 14.3 | 17.9 | 3.6 |
| Specimen-2 | 12.7 | 15.4 | 2.7 |
| Specimen-3 | 13.0 | 18.0 | 5.0 |
| Mean: | 13.3 | 17.1 | 3.8 |
| Std Dev: | 0.9 | 1.5 | 1.2 |

In certain embodiments, an RFID tag may be incorporated into the structure of the absorbent article. Alternatively, the RFID tag may comprise a reusable strip or patch that is attached to an outer surface of the absorbent article. As shown in FIG. 1, the absorbent article chassis 102 may define an attachment area 162 that includes mechanisms for attaching the sensor tag to the absorbent article. Such mechanisms may include hook-and-loop materials, including, for example, a loop material positioned on the absorbent article, with a hook element attached to a backside of the tag. Alternatively, the absorbent article may incorporate a plastic film covering the attachment area 162, and the tag may comprise an adhesive capable of attaching to the film. Other mechanical or adhesive may be used.

Embodiments of the tag may be used a minimum of two times and may be used many more times. The tag may be constructed so that it can be cleaned after every use with a cleaning agent designed to kill bacteria and neutralize other contagions or harmful substances. The tag may be made of materials that are significantly more robust than the materials used in the absorbent article that is intended for a single use.

Figure 5:
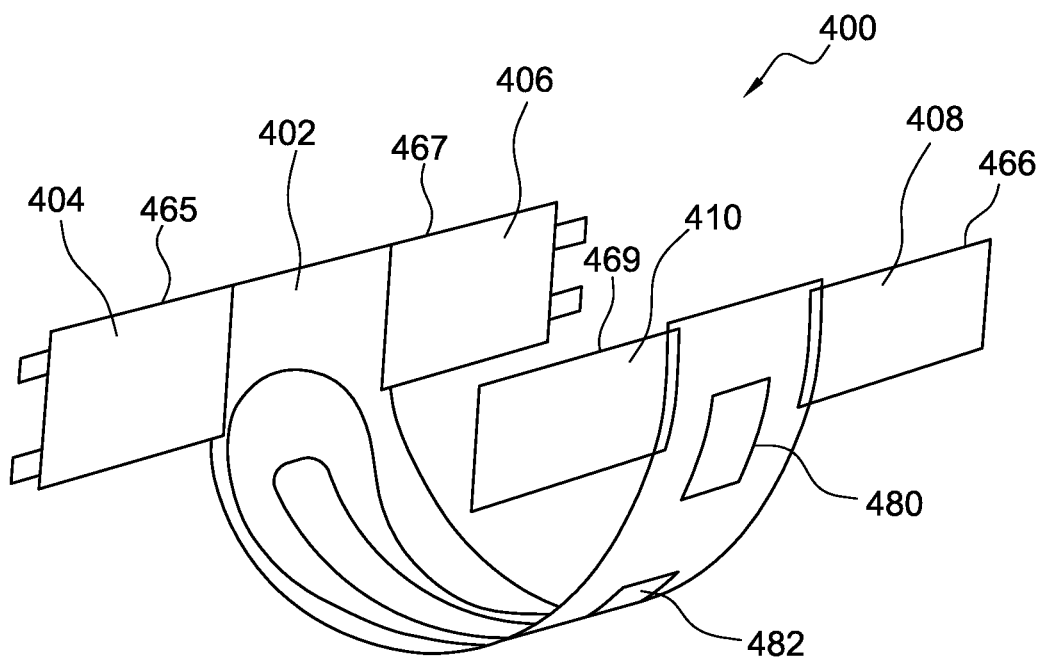
FIG. 5 illustrates a perspective view of an absorbent article in a second configuration.

FIG. 5 is a perspective view of an absorbent article 400 in a second configuration. Absorbent article 400 can be similar to and include similar components as absorbent article 100. By way of example, absorbent article 400 includes securement portion 404, 406, 408, and 410, which can be similar to securement portions 104, 106, 108, and 110, respectively. The second configuration shows the chassis 402 in a position as it would be when placed on the wearer although the securement portions, 404, 406, 408 and 410 remain in an un-contracted, unwrapped state. Securement portion 404 includes an edge 465, securement portion 406 includes an edge 467, securement portion 408 includes an edge 466, and securement portion 410 includes an edge 469. The chassis 400 may comprise a first set of indicia 480 indicating where the tag should be positioned on the outer cover of the chassis 402. The position of these indicia may be dependent on the size of the disposable article. In addition, the position may be dependent on whether the patient is male or female. For example, indicia 480 may be appropriate for a male patient. The outer cover may also include a second set of indicia 482 that the caregiver may use if the article is positioned on a female patient.

Figure 6:
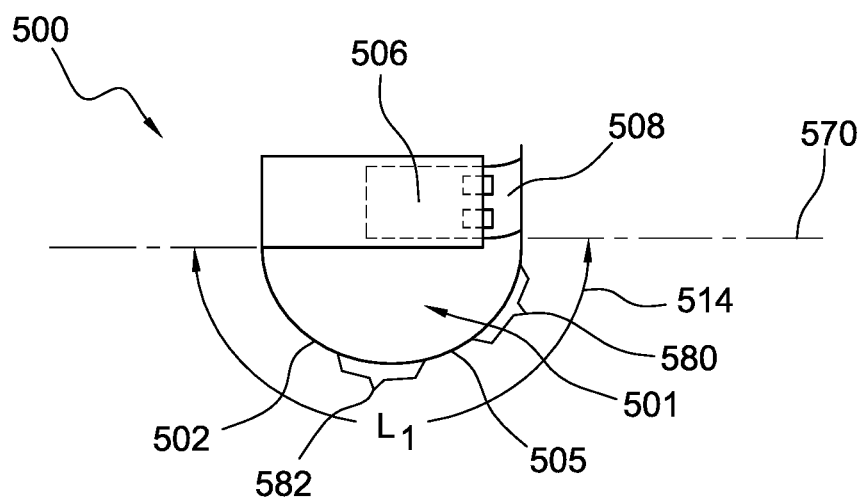
FIG. 6 illustrates a side view of an absorbent article in a third configuration.

FIG. 6 is a side view of an absorbent article 500 in a third configuration. Absorbent article 500 can be similar to and include similar components as absorbent article 100. By way of example, absorbent article 500 includes securement portion 504 (not shown), 506, 508, and 510 (not shown), which can be similar to securement portions 104, 106, 108, and 110, respectively. The third configuration shows the securement portions in a wrapped state, as they would be wrapped around a wearer. In this embodiment, the securement portions may be configured such that the second securement portion 506 overlaps the third securement portion 508, and the first securement portion 504 overlaps the fourth securement portion 510. The third and fourth securement portions 508, 510, lay directly adjacent the wearer's skin, while the first securement portion 504 and the second securement portion 506, lie partially on the wearer's skin and partially on the third and fourth securement portions respectively. Having front securement portions that may wrap substantially up to an in some embodiments substantially past a person mid point and around towards and against the wearer's backside provides a more comfortable fit. As discussed with respect to FIG. 5, the placement of the RFID tag may depend on the size of the absorbent article or the sex of the patient. Accordingly, indicia on the outer cover of the absorbent article 500 may indicate a first range of placement 580 or a second range of placement 582 for the tag.

Figure 7:
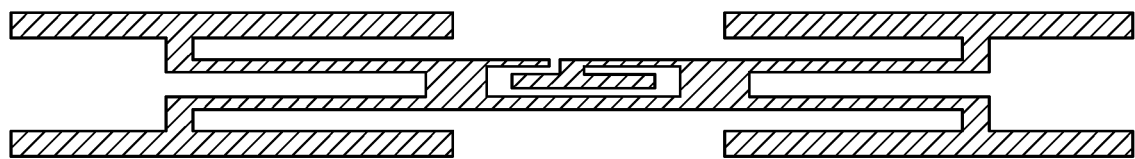
FIG. 7 illustrates an RFID tag antenna configuration in accordance with embodiments of the invention.
Figure 8:
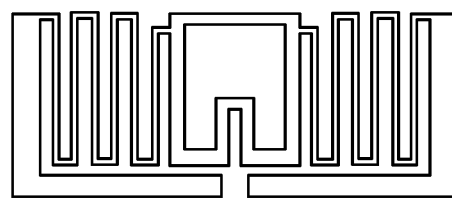
FIG. 8 illustrates an RFID tag antenna configuration in accordance with embodiments of the invention.
Figure 9:
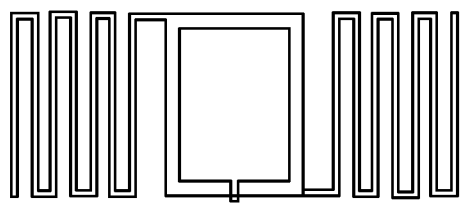
FIG. 9 illustrates an RFID tag antenna configuration in accordance with embodiments of the invention.
Figure 10:
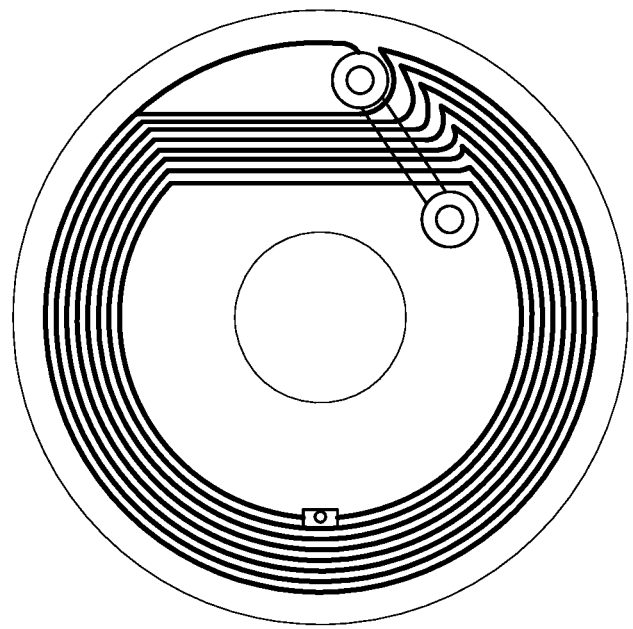
FIG. 10 illustrates an RFID tag antenna configuration in accordance with embodiments of the invention.
Figure 11:
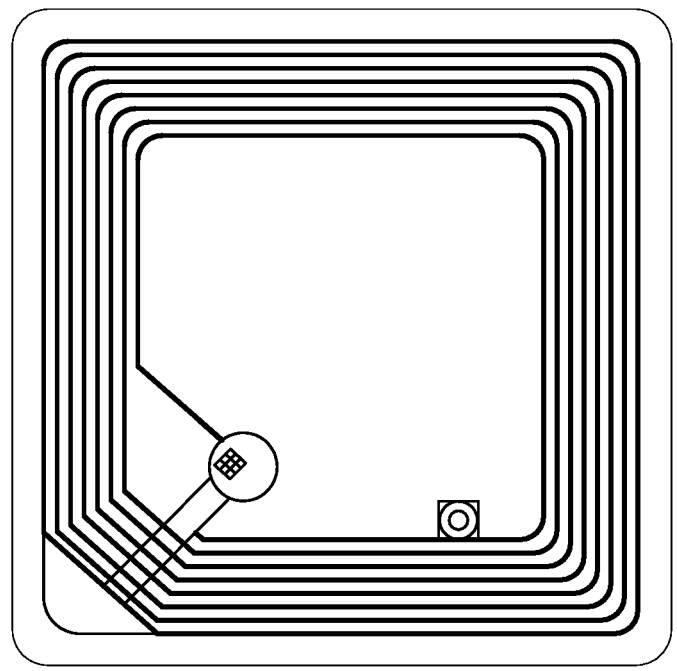
FIG. 11 illustrates an RFID tag antenna configuration in accordance with embodiments of the invention.

Embodiments of the tag may include various antenna configurations. For example, FIG. 7 shows a diagram of an embodiment of tag antenna. In the embodiment, the antenna is a dipole antenna where the radiating elements are the metal sheets extending in two directions and are looped around. FIGS. 8-11 illustrate other possible antenna configurations as would be understood by one of ordinary skill in the art.

In addition, the placement of the tag position indicia may depend on the type, level of absorbency, materials and other characteristics of the absorbent article. In addition, other factors may be taking into consideration, including the intended length of use, or the age, sensitivity, or medical conditions of the patient. The tag may also be placed such that the tag may also determine level of wetness in the absorbent article. For example, the impedance sensed by the tag may have a certain value if the absorbent article is at 10% of its capacity. The tag may report this impedance level and the reader may display to the caregiver that the absorbent article is at 10% capacity. Impedance values may be similarly mapped up to 100%, with the reader indicating the value to the caregiver. At 100%, or some level approaching 100%, the reader may indicate that a change of the absorbent article is required immediately to avoid leakage.

Embodiments of the RFID reader may be incorporated into one or more of various devices. An RFID reader, also known as an interrogator, may be a stand-alone device or may provide a connection between the tag data and a networked system. Embodiments of the reader use an attached antenna to capture data from tags. The reader may then passes the data to a computer, hand held device, network or other machine for processing. Embodiments of the reader can be affixed in a stationary position, integrated into a mobile device such as a portable, handheld scanner, tablet, mobile phone or other device. Alternatively, embodiments of the reader may be incorporated in a wristband, badge or the like worn by a caregiver or the reader may be affixed to a movable cart or other equipment used by the caregiver.

Upon attachment to the diaper, the sensor may also transmit information indicating that the sensor has been attached to a diaper and regarding the diaper size or other characteristics to the reader. The reader itself may display this information or the information may be displayed on a remote display device. The reader and/or remote display device may be a software application ("app") running on a mobile electronic device, such as a mobile phone or similar. The app may display the size of diaper to which the sensor has been attached. The app may also compare the size of diaper to which the sensor has been attached with data entered regarding the intended size for the patient and thereby verify that the size of diaper that has been put on the patient is the size of diaper that should have been used for the patient. The app may include a visual or audible acknowledgement to indicate the correct diaper size has been used. In addition, the reader or remote display may indicate the date and time that the absorbent article was put on the patient, the date and time that the article was last checked and whether the absorbent article needs to be changed.

Figure 12:
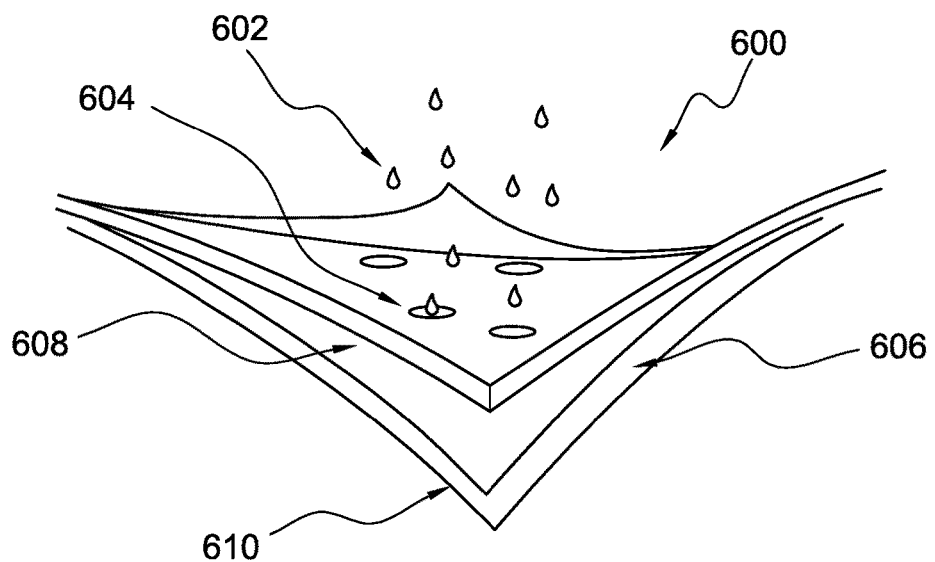
FIG. 12 shows a cross-section of an embodiment of an absorbent pad of the present invention.
Figure 13:
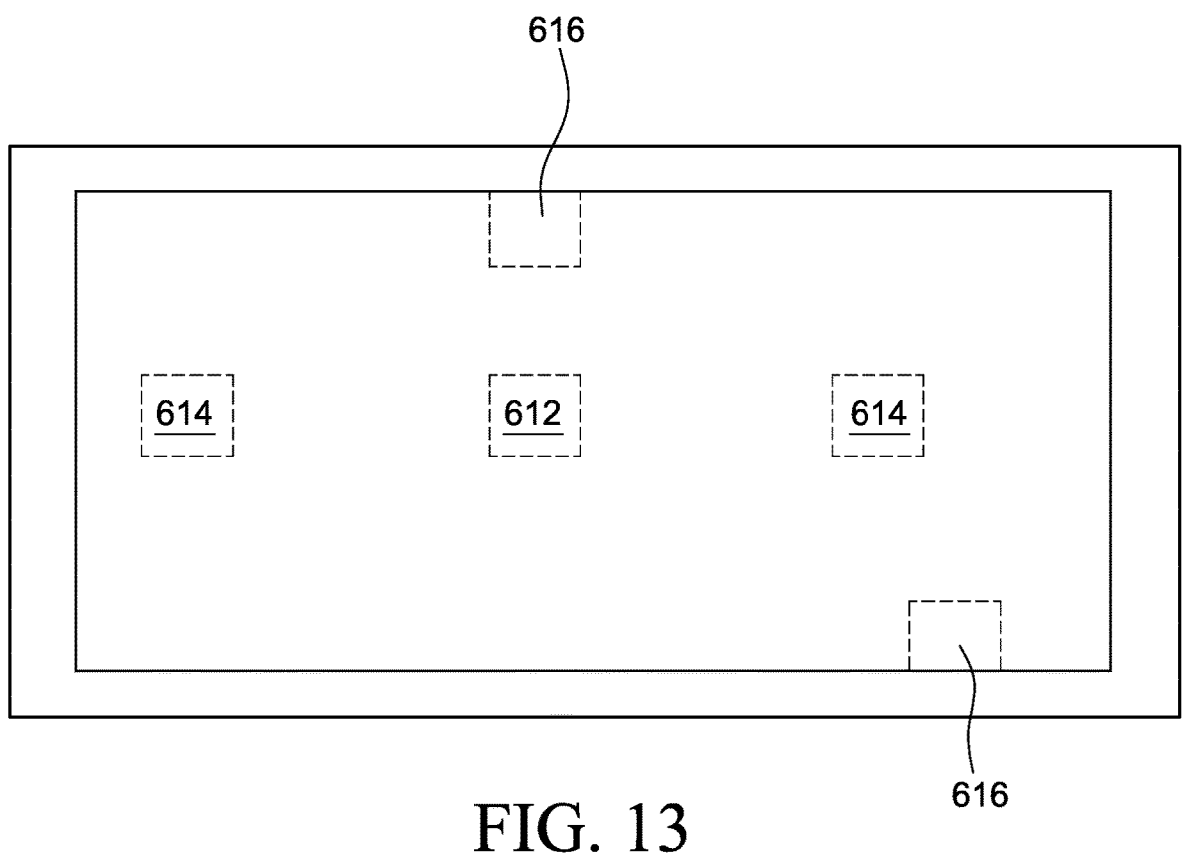
FIG. 13 shows a top view of an embodiment of the absorbent pad of FIG. 12.

As illustrated in FIGS. 12-13, in various embodiments, sensors and RFID tags of the present invention may be used in conjunction with an absorbent pad 600 comprising multiple layers, e.g., three or more layers, wherein the first layer 602 is comprised of a fluid-permeable, porous material, the second layer 604 is disposed under the first layer and is comprised of at least one super absorbent material, and a base layer 606 disposed under the second layer.

In certain embodiments of the invention, the base layer 606 is comprised of a third layer 608 comprised of a hydrophobic, breathable film, disposed under the second layer and a fourth layer 610, disposed under the third layer, comprised of an air-permeable material.

In one embodiment of the invention, the first layer is a nonwoven material. The nonwoven material of the first layer can be manufactured using any technique known in the art. Non-limiting examples of suitable types of nonwoven materials include staple nonwoven materials, melt-blown nonwoven materials, spunmelt nonwoven materials, spunbond nonwoven materials, SMS (spunbond meltblown spunbond) materials, spun lace materials, needle-felted materials, thermal-bonded nonwoven materials, trough-air-bonded nonwoven material, spunlaid nonwoven material, air-laid nonwoven materials or the like, or any combinations thereof.

In certain embodiments of the invention the first layer 602 is hydrophilic. For example, the first layer can be treated in order make it fluid permeable. Such treatments can include any treatment known in the art, which renders a material fluid permeable.

In another embodiment of the invention, the first layer is permeable to fluids such that the fluids can pass through the surface of the first layer toward the second layer (disposed beneath the first layer), but the fluids cannot substantially reverse direction and move back toward the surface of the first layer. In other words, in various embodiments the flow of fluids through the first layer is substantially unidirectional from the top surface of the first layer toward the second layer disposed beneath the first layer.

The first layer can comprise any suitable material known in the art. For example, the first layer can comprise a polymeric material. Non limiting examples of such polymeric materials include polypropylene, polyethylene, polyethylene terephthalate, polyamide, viscose rayon, nylon, or the like or any combinations thereof. Furthermore, the polymeric material can be a biodegradable polymeric material.

The second layer 604 of the absorbent pad of the present invention is disposed beneath the first layer 602. For example, the second layer can be located directly beneath the first layer and in direct contact with the first layer, or adhered to the first layer by means of one or more intervening layers, for example an adhesive layer and/or a spacer layer.

In certain embodiments the second layer is comprised of a formed material. The formed material of the second layer can be manufactured using any technique known in the art. Non-limiting examples of suitable types of formed materials include staple nonwoven materials, melt-blown nonwoven materials, spun-melt nonwoven materials, spun-bound nonwoven materials, thermal-bonded nonwoven materials, trough-air-bonded nonwoven materials, spun-laid nonwoven materials, air-laid nonwoven materials, or any combinations thereof. In a particular embodiment the second layer is comprised of an air-laid fiber. In one embodiment the air-laid fiber is thermobonded. In a particular embodiment the air-laid material is air laid paper.

The second layer can comprise fibers, for example natural fibers. The natural fibers can be any suitable natural fibers known in the art. In one embodiment the natural fiber is cellulose. The cellulose can be from any suitable source known in the art. Non-limiting examples of suitable sources of cellulose are wood fibers, plant fibers, field crop fibers, fluff pulp fibers, cotton, any other material, man-made or natural, designed to absorb fluid, or any combination thereof. In a particular embodiment the second layer comprises wood fibers. In another embodiment, the second layer comprises macerated wood pulp. The second layer of the pad can further comprise an absorbent polymer, for example any super-absorbent polymer known in the art. In a particular embodiment, the second layer is a thermobonded, absorbent airlaid core made from cellulose fibers and super-absorbent polymers.

The second layer absorbs substantially all of the fluids penetrating through from the first layer, and has a fluid-holding capacity sufficient to retain fluids without releasing the fluid through the first layer or through the third and fourth layers. In a particular embodiment of the present invention, the second layer can be comprised of more than one fluid absorbing layer (also known as "core" layers). For example, the second layer can comprise two (or more) layers, each comprising the same or different absorbent polymer.

In certain embodiments of the invention, the base layer 606 is comprised of a third and fourth layer, wherein the third layer is disposed under the second layer and the fourth layer disposed under the third layer.

The base layer 606 (or in certain embodiments, the third layer 608) prevents the fluid absorbed in the second layer to penetrate through the base layer of the absorbent pad (or in some embodiments, the fourth layer 610). The base layer can comprise any natural or man-made material capable of preventing the flow of fluids out of the second layer and through the bottom of the absorbent pad. In certain embodiments wherein the base layer 606 comprises a third 608 and fourth 610 layer, the third layer comprises a polymeric film, for example a hydrophobic polymeric film. The polymeric film of the third layer can be any suitable polymer known in the art, for example suitable hydrophobic polymers.

The base layer should also provide for air circulation within the absorbent pad to prevent heat and moisture vapor build up. Accordingly, in particular embodiments, the base layer is air permeable. Air permeability can be provided in various ways, for example by forming a base layer comprising a third layer and fourth, wherein the third layer comprises a woven or nonwoven hydrophobic material which prevents the movement of bulk fluid, but allows diffusion or movement of air through the third layer. Although the base layer does not permit any appreciable amount of liquid to flow through, in many instances it can be advantageous to allow moisture vapor to permeate through the base layer.

In an embodiment of the invention, the fourth layer 610 is a non-woven material. The non-woven material of the fourth layer can be manufactured using any technique known in the art. In certain embodiments of the invention the fourth layer is hydrophobic. The fourth layer can be made of any suitable material known in the art.

As illustrated in FIG. 13, one or more sensors and/or RFID tags may be placed on or in the absorbent pad 600. These sensors may be placed at different positions within the pad to convey information to the caregiver. For example, a sensor 612 may be placed generally in the center of the pad between the first and second layers. The sensor may include a wetness sensor as described above. In this manner, the caregiver can be alerted if the absorbent pad is subject to any fluid insult. Alternatively, the sensor may be placed below the second layer 604 and above the third layer 608 such that information on wetness is conveyed to the caregiver after the fluid has absorbed through the second layer. The sensor 612 may also be placed in a location that is not the center of the pad but is the location most likely to first be exposed to fluid.

Additional sensors 614 may be placed a farther distance from the center of the absorbent article to provide information to the caregiver regarding the spread of fluid within the pad 600. Alternative or additional sensors 616 may be placed adjacent to an edge of the pad to provide the caregiver with information indicating that fluid has or will soon reached an edge of the pad.

The various sensors 612, 614, 616 incorporated in the pad 600 may be RFID tags as described above to identify wetness or moisture in the pad. Alternatively or in conjunction with the wetness sensor, the sensors may incorporate sensors that provide information regarding temperature and/or pressure within the pad. These additional sensors may be used in conjunction with an RFID tag or other device for communicating the information sensed by the sensors.

In further embodiments, a pad 600 of the present invention may be integrated with a sheet with fitted corners, sized to fit an operating room table, stretcher, bed or other patient support structure. The sheet may comprise a resilient material such as an elastic cord, string or tape that is connected to an edge of the flexible sheet material in such a way that it gathers the flexible material into a fitted end or corner that would allow the user to tuck the corners of the sheet around a mattress pad or other support structure in order to secure the sheet and pad against movement relative to the support surface.

In a further embodiment of the invention, the pad extends across substantially the entire area of the sheet, the pad providing the flexible material for forming the fitted corners. In an alternative embodiment, the sheet may be formed by extending the first layer or topsheet, described above and shown in FIG. 12, beyond the perimeter of the other layers of the pad such that the extended portion of the topsheet provides the flexible material that is used to form the fitted corners. In another embodiment, the sheet may be formed by extending the fourth layer or backsheet, described above and shown in FIG. 12, beyond the perimeter of the other layers of the pad such that the extended portion of the backsheet provides the flexible material that is used to form the fitted corners. In a further embodiment, the pad may be joined to a section of additional material that surrounds one or more edge of the pad in order to provide the flexible material used to form the fitted corners. This additional material may be any appropriate flexible material and may be fluid-permeable or non-fluid-permeable. In yet another embodiment, the sheet may be formed by providing a flexible sheet having fitted corners and securing a pad, as described herein, to an upper or lower surface of the flexible sheet. The pad may be secured to the sheet by adhesive, thermal or ultrasonic bonding, mechanical engagement or by any other appropriate means to connect the pad with the sheet as would be apparent to one of ordinary skill in the art.

In an embodiment of the invention, the pad may be sized such that it covers substantially the entire upper surface of the patient support structure. In other embodiments, the pad may be smaller in area than the upper surface of the support structure. In certain embodiments, the pad may be located within the sheet such that the pad is positioned on an area of the support structure more likely to be wetted with fluids.

Figure 14:
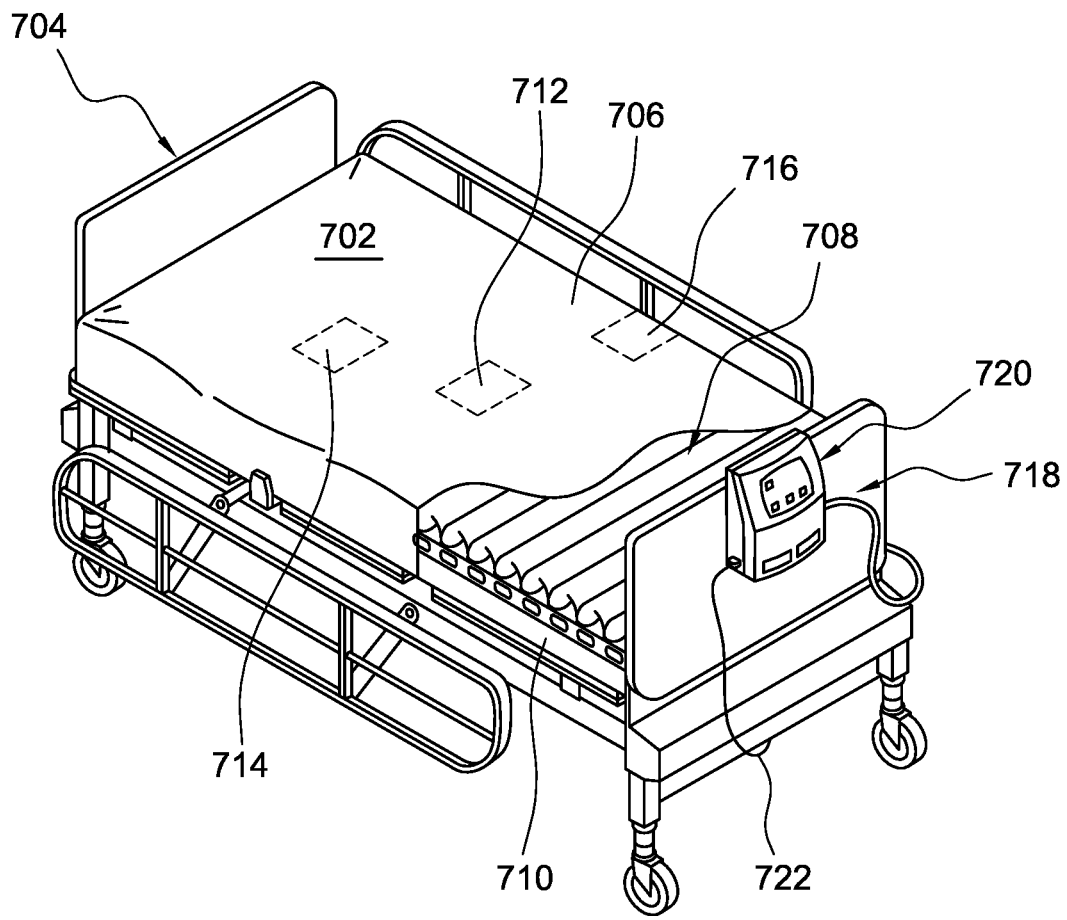
FIG. 14 is a partially cutaway, perspective view of a mattress and bed frame in accordance with embodiments of the invention.

In further embodiments of the invention, sensors and/or RFID tags may be used in conjunction with a mattress. FIG. 14 shows a mattress 702 and hospital style bed frame 704. The mattress 702 includes a mattress cover 706 and an internal mattress structure. The internal mattress structure may include a padded topper portion 708 and a lower structural support portion 710. An RFID tag or one or more sensors may be incorporated into the mattress 702. In an embodiment, a first sensor 712 is positioned in a generally central portion of the mattress in a position most likely to experience a fluid insult. The sensor may be positioned immediately below the cover 706 and above the padded portion 708. Alternatively, the sensor 712, or an additional sensor, may be positioned below the padded portion but above the structural portion 710 of the mattress. A sensor placed just below the cover may provide the caregiver or mattress supplier with information when fluid penetrates the mattress cover. A sensor positioned below the padded portion 708 may provide the caregiver or mattress supplier with information when fluid penetrates more deeply into the mattress.

Additional sensors 714 may be placed a farther distance from the center of the mattress to provide information to the caregiver regarding the spread of fluid within the mattress 702. Alternative or additional sensors 716 may be placed adjacent to an edge of the mattress to provide the caregiver with information indicating that fluid has or will soon reached an edge of the mattress. An array of tags may be used to ensure the high priority sites of the mattress are monitored.

The various sensors 712, 714, 716 incorporated in the mattress 702 may be RFID tags as described above to identify wetness or moisture in the pad. Alternatively or in conjunction with the wetness sensor, the sensors may incorporate sensors that provide information regarding temperature and/or pressure within the pad. These additional sensors may be used in conjunction with an RFID tag or other device for communicating the information sensed by the sensors. For example, the sensors may incorporate one or more RFID tags that are regularly scanned by a caregiver with a hand held, bed mounted or built in to the mattress reader.

In embodiments of the mattress, the sensors may be connected wirelessly or by wires 718 to an electronics module 720 attached to the bed frame 704. The electronics module may act as a data logger to interrogate the tag(s)/ sensors on a regular basis to determine if moisture has leak through to the foam. Once moisture has been detected, an alert light or some sort of visual indicator is turned on. In alternative embodiments, the electronics module may be a built-in module (not shown) incorporated into the mattress itself.

The use of RFID tags or other wireless sensors in the mattress may provide an advantage relating to the ease of assembly of the mattress and lack of introduction of new pressure points in the mattress by the wires. Alternatively, the use of wired sensors and an external electronics module allows the module/sensors to be powered by a wired connection 722 to an external power supply.

Figure 15:
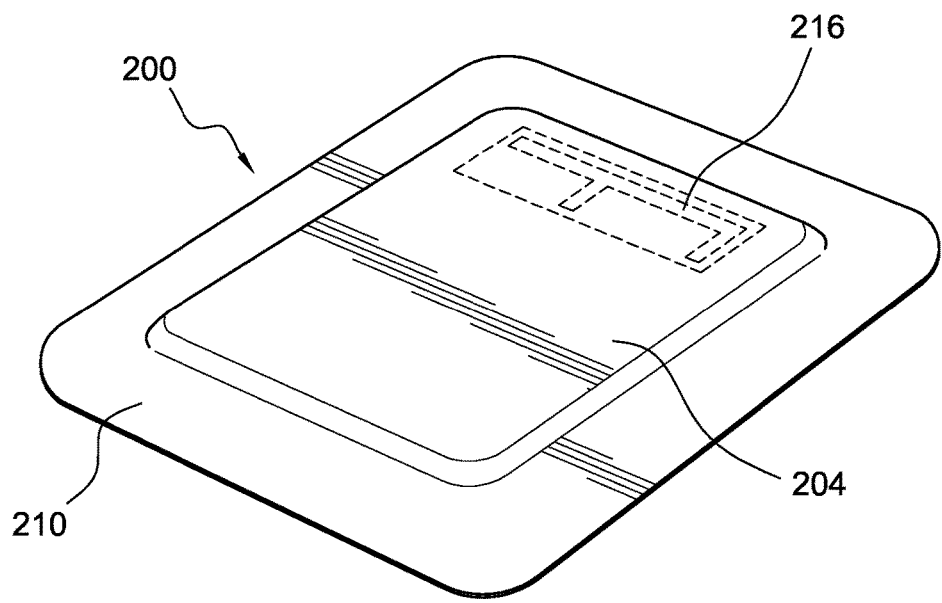
FIG. 15 is a perspective view of a wound dressing in accordance with embodiments of the invention. Portion of the dressing have been removed to show interior features.
Figure 16:
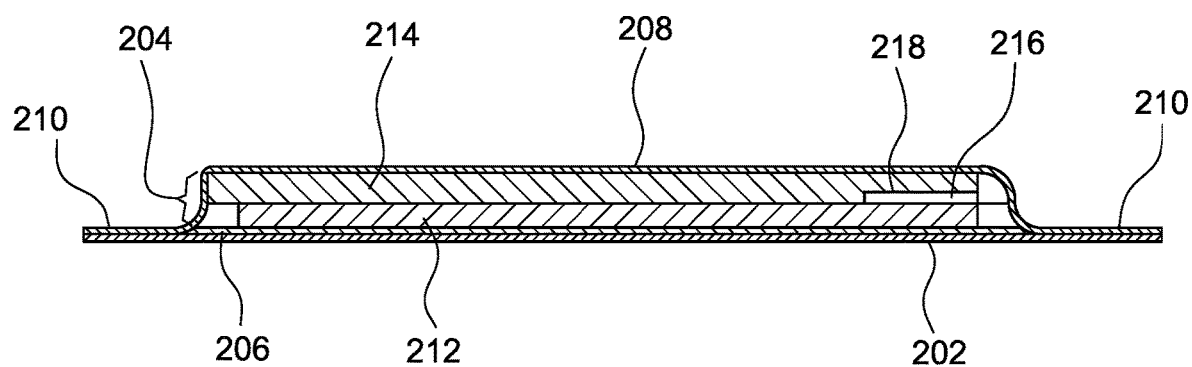
FIG. 16 is a cross-sectional view of the wound dressing of FIG. 15.
Figure 17:
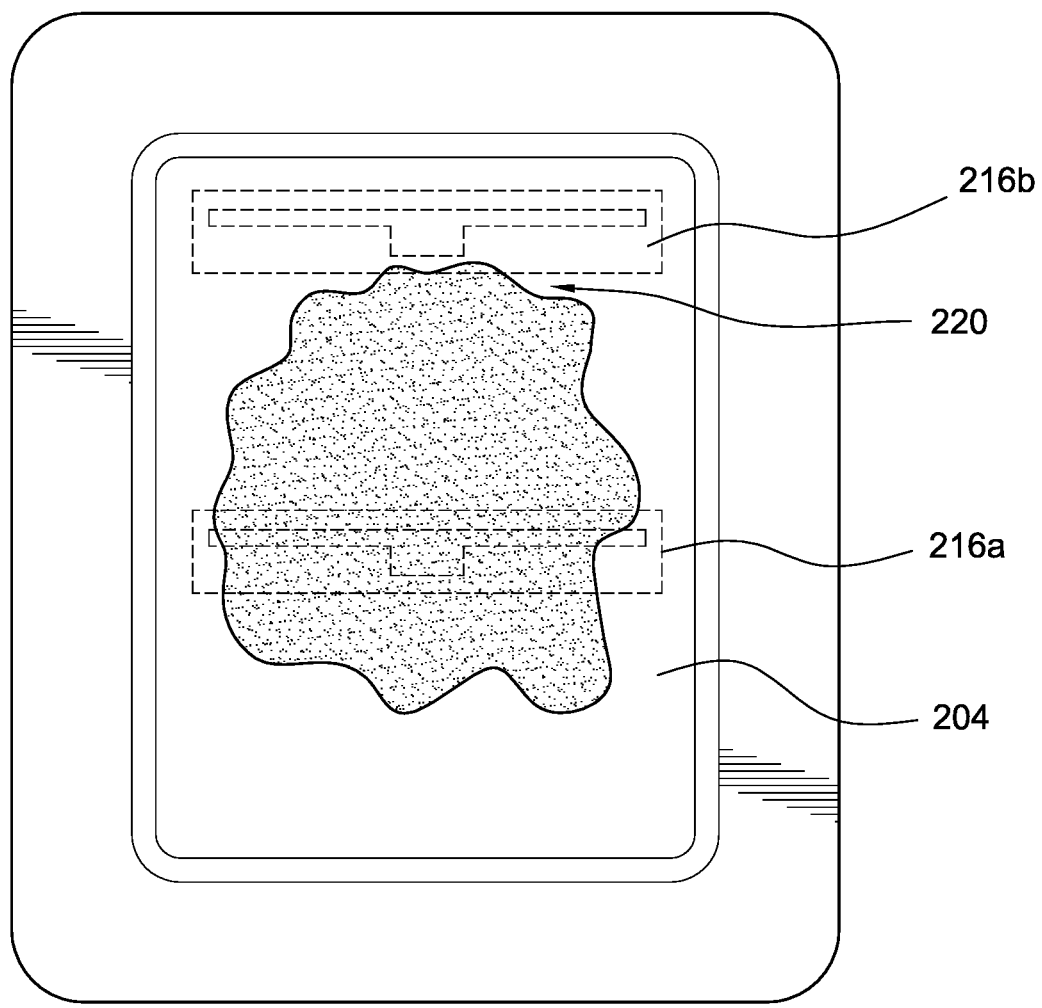
FIG. 17 is a top view of the wound dressing of FIG. 15. Portion of the dressing have been removed to show interior features.

FIGS. 15-17 illustrate further embodiments. A wound dressing 200 may comprise a wound contact layer 202, and absorbent core 204, and a cover layer 208. The wound contact layer 202 may be positioned over a patient's wound such that wound exudate is transferred through the wound contact layer to an absorbent core 204. The wound contact layer may be formed of silicone or another appropriate material such as a polymer film. In further embodiments, the wound contact layer may comprise a laminate of silicone backed by a polymer film. For example, a polyurethane film may be used. The silicone and film laminate may be perforated to allow passage of exudate from the wound to the absorbent core 204. The cover layer may extend beyond and enclose the absorbent core 204 and seal against the wound contact layer 202 in a frame area 210 that surrounds the absorbent core. The cover layer 208 may be formed of polyurethane or another appropriate material. Preferably, the cover layer is vapor permeable but liquid impermeable. In this manner, exudate may be contained by the dressing but allowed to evaporate through the cover layer.

The silicone may be a silicone adhesive that serves to adhere the dressing to the patient's skin. The wound contact layer may have an adhesive, such as an acrylic adhesive, positioned on the back side of the layer to adhere the wound contact layer to the remainder of the dressing. Alternatively, the wound contact layer 202 may be adhered only to the cover layer 208 in the frame area 210. A separation layer 206 may be positioned between the wound contact layer 202 and the absorbent core 204. The separation layer may be formed by a polymer film or mesh, a woven material, such as a textile fabric, or a paper material, such as tissue paper. The separation layer may serve to isolate the wound contact layer from the absorbent core such that exudate can pass from the wound contact layer to the absorbent core, but contaminants and particulates cannot pass in the other direction.

The absorbent core 204 may comprise lower 212 and upper 214 layers. In various embodiments, the first layer may comprise a superabsorbent substance. Superabsorbent substances may comprise materials being able to absorb and retain large volumes of water in aqueous solutions. Superabsorbent substances falling into this category are for example modified starch, polymerized polyvinyl alcohol (PVA) and polyethylene oxide (PEO), which are all hydrophilic and have a high affinity to water. In a particular embodiment of the present invention, the superabsorbent substance is a superabsorbent polymer (SAP), in particular in the form of (granular) particles or fibers. In an embodiment, such a SAP is made from polymerization of acrylic acids blended with sodium hydroxide in the presence of an initiated form poly-acrylic acid sodium salt (sometimes referred to a sodium poly-acrylate).

In a further embodiment, first layer 212 containing SAP comprises a carrier layer, wherein the superabsorbent polymer is dispersed in the carrier layer. In an embodiment, the carrier layer in particular may comprise, for example, tissue paper, a spunlaced polymer, a non-woven fabric, fluff/cellulose, regenerated cellulose as rayon, foam based on different chemistry as polyurethane, alginate, hydrocolloid, carboxymethyl cellulose (CMC) and its derivate or cotton.

In an embodiment, lower layer of the absorbent core may comprise a laminate structure. The SAP is dispersed on a lower laminate layer, then an upper laminate layer is put on top and the two laminate layers are consolidated providing a matrix carrying the SAP between the two layers. In further embodiments, the lower layer 212 comprises a carrier layer made of a spunlaced polymer as a non-woven fabric and a granular or fibrous SAP. The SAP is dispersed on a first sheet or layer of the spunlaced nonwoven. A second sheet or layer of the spunlaced nonwoven is put on top of the first sheet, such that the SAP is located between the two sheets or layers. The SAP may be integrated in both layers by applying pressure to this sandwich structure provided. By applying pressure, the two layers of spunlaced polymer are consolidated and the SAP to some extent fills up voids in the spunlaced material. In a further embodiment, the lower absorbent core layer 212 may comprise a polyurethane film or other absorbent material with a layer of SAP paper laminated or otherwise attached to an upper surface of the absorbent material. In still further embodiments, the lower layer may comprise a fibrous or fluff material with SAP granules dispersed throughout the material. The SAP granules may be dispersed evenly or may be more concentrated in certain portions, such as in the center of the dressing or in a lower portion of the lower layer.

The upper layer 214 of the absorbent core 202 may comprise an absorbent material in contact with the cover layer 208 that allows fluid absorbed by the dressing to evaporate through the vapor permeable cover layer. The upper layer 214 may comprise, for example, tissue paper, a spunlaced polymer, a non-woven fabric, fluff/cellulose, regenerated cellulose as rayon, foam based on different chemistry as polyurethane, alginate, hydrocolloid, carboxymethyl cellulose (CMC) and its derivate or cotton.

An RFID tag or one or more sensors may be incorporated into the wound dressing 200. In embodiments, a first sensor 216 may be positioned immediately below the cover layer 208 and above the upper absorbent core layer 214. Alternatively, the sensor 216, or an additional sensor 216a, may be positioned between the upper 214 and lower 212 layers of the absorbent core 204. The sensor 216 may be placed on an upper surface of the lower layer 212 and a portion 218 of the upper layer 214 may extend over a top surface of the sensor.

As illustrated in FIG. 17, a first sensor 216a may be positioned in a generally central portion of the wound dressing in a position most likely to first encounter wound exudate. The sensor 216a or an additional sensor 216b may be placed adjacent an edge of the absorbent core 204. In this manner, if one sensor 216a positioned generally in the center of the dressing is used, the sensor 216a senses the exudate when it is initial present in the dressing, and the caregiver receives information indicating that an initial exudate is present in the dressing. If one sensor 216b is used positioned at adjacent an edge of the dressing, as an edge of the area wetted by exudate 220 reaches the sensor 216b, information can be communicated to the caregiver that wound dressing is reaching its absorbent capacity. Alternatively, if more than one sensor is used, as the first sensor 216a is wetted, the caregiver receives information indicating that exudate is present in the dressing, and as the an edge of the area wetted by exudate 220 reaches the sensor 216b, information can be communicated to the caregiver that wound dressing is reaching its absorbent capacity.

The sensor 216 incorporated in the wound dressing 200 may be an RFID tag as described above to identify wetness or moisture in the dressing. Alternatively or in conjunction with the wetness sensor, the sensors may incorporate sensors that provide information regarding temperature and/or pressure within the pad. These additional sensors may be used in conjunction with an RFID tag or other device for communicating the information sensed by the sensors. For example, the sensors may incorporate one or more RFID tags that are regularly scanned by a caregiver with a hand held reader. Alternatively, a reader may be built into a bed or other structure used to support the patient.

Figure 18:
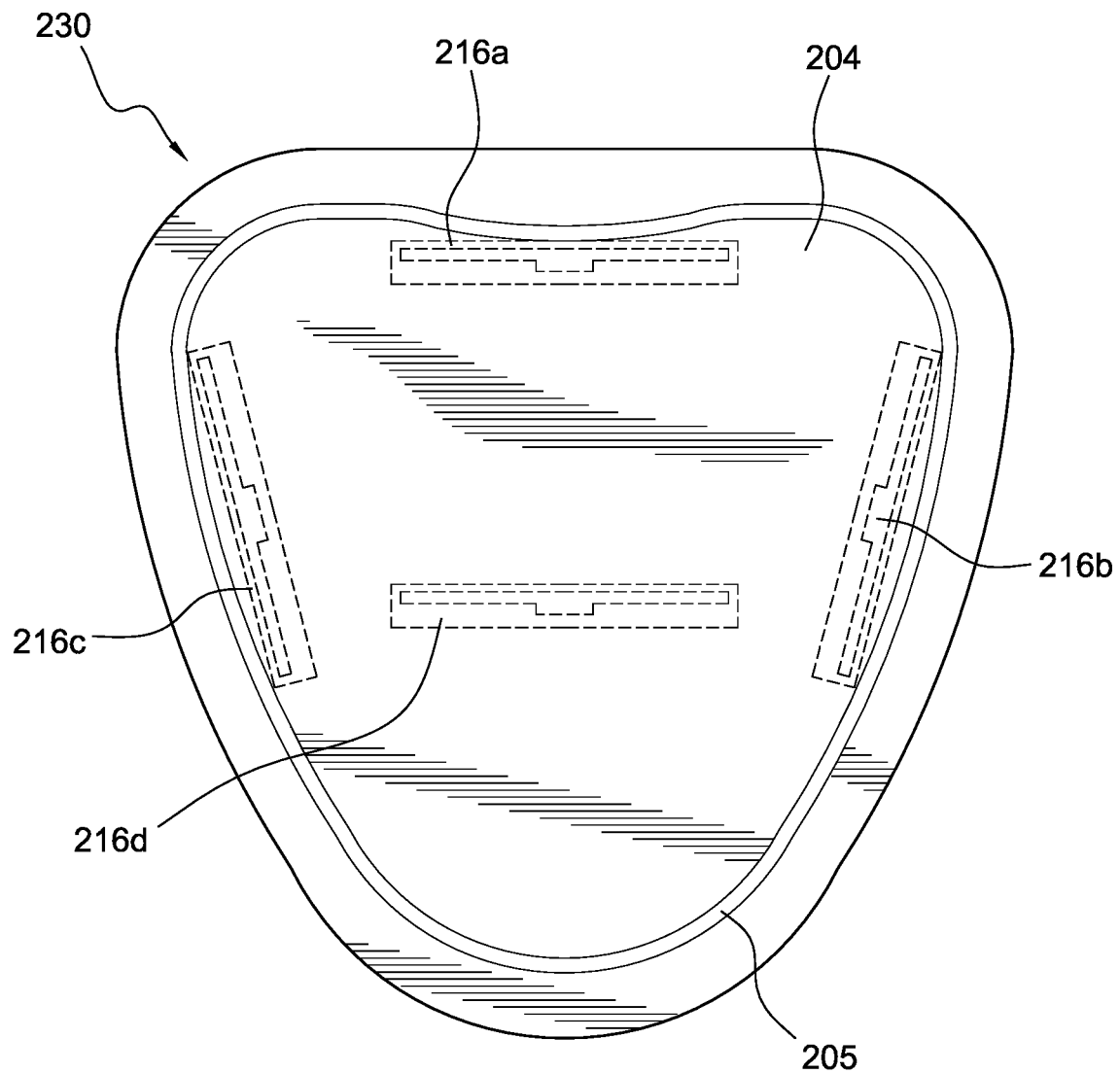
FIG. 18 is a top view of a further embodiment of a wound dressing in accordance with embodiments of the invention.

In larger wound dressings, such as the sacral wound dressing 230 shown in FIG. 18, multiple sensors 216a-d may be used. The sensors may be distributed at various locations throughout the absorbent core 204. For example, as illustrated, a sensor 216d may be positioned generally in the center of the dressing or in a position within the dressing that is likely to be the first position to be wetted by exudate. Additional sensors 216a-c may be positioned at various spaced apart locations adjacent to an edge 205 of the absorbent core 204. In this manner a caregiver may receive information indicating the initial wetting of the dressing and/or information that the area wetted by the exudate has or will soon reached an edge of the absorbent core.

Figure 19:
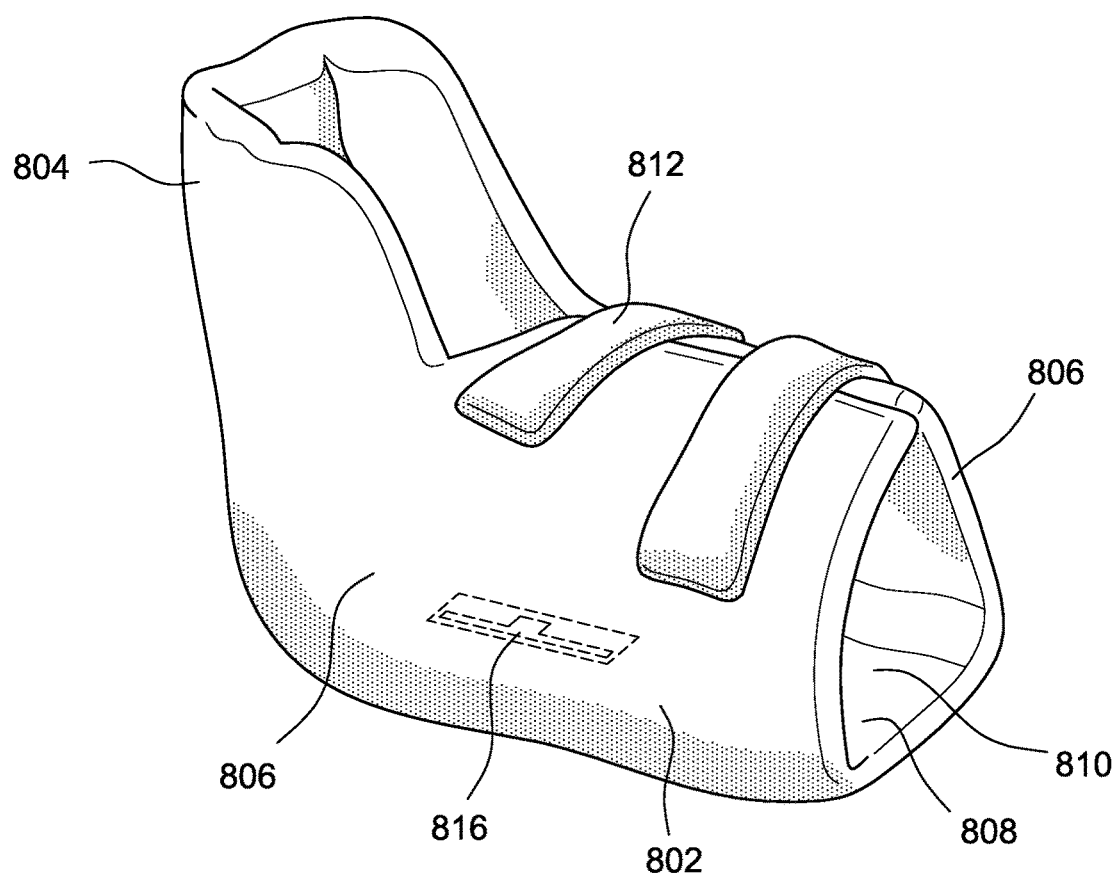
FIG. 19 is a perspective view of a heel protector in accordance with embodiments of the invention.

In further embodiments of the invention, as illustrated in FIG. 19, a heel protection device is provided. The device serves to protect a patient's heels against the formation of pressure ulcers. Embodiments of the heel protectors comprise a generally boot shaped portion 802. The boot may include a lower portion 804 positioned below the sole of the patient's foot, side portions 806 that extend along the side of the foot and up over the ankle and lower leg, and a rear portion 808 that extents along the heel, ankle and lower portion of the leg. This rear portion 808 supports and cushions the heel from contact with the bed. One or more straps 812 secure the heel protector to the patient's foot.

In embodiments, a sensor 816 may be positioned on an inside surface 810 of the rear support portion 808. The sensor may be positioned adjacent or immediately below the patient's heel. The sensor 816 incorporated in the heel protector may be an RFID tag as described above to identify wetness or moisture in the dressing. Alternatively or in conjunction with the wetness sensor, the sensors may incorporate sensors that provide information regarding temperature and/or pressure within the protector. These additional sensors may be used in conjunction with an RFID tag or other device for communicating the information sensed by the sensors. For example, the sensors may incorporate one or more RFID tags that are regularly scanned by a caregiver with a hand held mattress reader. Alternatively, a reader may be built into a bed or other structure used to support the patient.

Figure 20:
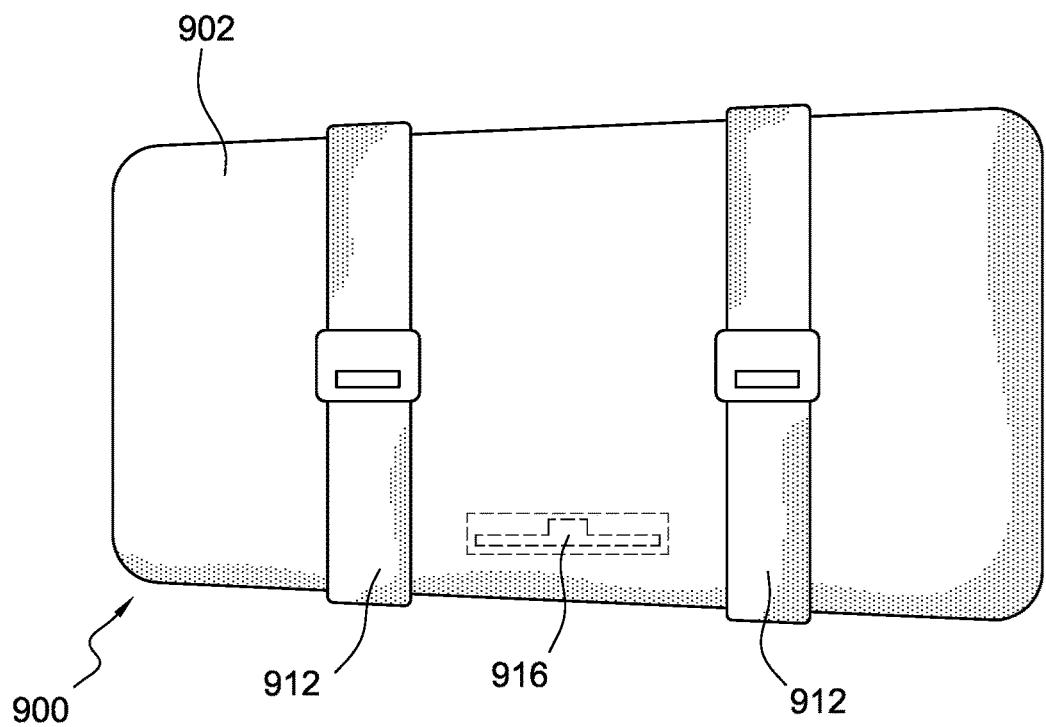
FIG. 20 is a side view of a compression garment in accordance with embodiments of the invention.

In further embodiments of the invention, as illustrated in FIG. 20, sleeve or other compression garment may be provided for the treatment of deep vein thrombosis (DVT). The device serves to provide compression for the treatment of DVT and may encircle a patient's limb. In particular, DVT garments may be used to apply treatment to a patient's foot, calf, thigh or entire leg. Embodiments of the compression garment 900 comprise a sleeve portion 902. The sleeve surrounds at least a portion of a patient's leg. One or more fasteners or straps 912 secure the sleeve. One or more bladders within the sleeve are pressurized to provide compression. The sleeve may comprise a structural outer portion and an inner liner of softer material that contacts the patient's skin. One or both of the inner liner and structural portion may comprise a breathable material.

In embodiments, a sensor 916 may be positioned on an inside surface of the sleeve 902. The sensor may be positioned on an inside surface of the inner liner or between the liner and the structural portion of the sleeve. The sensor 916 may be an RFID tag as described above to identify wetness or moisture in the dressing. Alternatively or in conjunction with the wetness sensor, the sensors may incorporate sensors that provide information regarding temperature and/or pressure within the protector. These additional sensors may be used in conjunction with an RFID tag or other device for communicating the information sensed by the sensors. For example, the sensors may incorporate one or more RFID tags that are regularly scanned by a caregiver with a hand held mattress reader. Alternatively, a reader may be built into a bed or other structure used to support the patient.

Embodiments of the invention include, an absorbent structure comprising: a liquid permeable layer; a liquid impermeable layer; an absorbent layer positioned between the liquid permeable layer and the liquid impermeable layer; a first sensor positioned between the liquid permeable layer and the liquid impermeable layer; and a second sensor positioned between the liquid permeable layer and the liquid impermeable layer; wherein the second sensor is separated from the first sensor by a first distance, and wherein the second sensor is positioned closer to a periphery of the absorbent structure than the first sensor.

Further embodiments may include an absorbent structure wherein the liquid impermeable layer is breathable or wherein the absorbent layer comprises a superabsorbent substance, which may be a superabsorbent polymer.

In further embodiments, the first sensor may be positioned between the liquid permeable layer and the absorbent layer, between the absorbent layer and the liquid impermeable layer or within the absorbent layer. Additionally, the second sensor likewise be positioned between the liquid permeable layer and the absorbent layer or between the absorbent layer and the liquid impermeable layer. In particular embodiments, the first sensor is positioned between the liquid permeable layer and the absorbent layer while the second sensor is positioned between the absorbent layer and the liquid impermeable layer.

The absorbent structure may comprise any number of absorbent structures for use absorbing liquids emitted by patients, including incontinence articles, wound dressings, mattresses, absorbent pads for placing below a patient, such as on a mattress, hygienic pads, including feminine hygienic pads, as well as other absorbent structures for use in providing care for patients.

The absorbent structure may also comprise an RFID tag, and the sensors may comprise an RFID moisture sensor. Embodiments of the RFID moisture sensor may comprise a tail, an antenna coupled to the tail, a processing module, and a wireless communication module. The coupled tail may have an impedance that varies with an environmental condition in which the antenna and the tail are placed. The environmental condition may be temperature, humidity, wetness, or proximity of an RFID reader to the RFID sensor.

In further embodiments of the absorbent structure, the absorbent structure may be as described above with the first sensor positioned within the absorbent structure first area and with the second sensor separated from the first sensor by a first distance, wherein the second sensor is positioned outside the absorbent structure first area. In such embodiments, the second sensor may be positioned closer to a periphery of the absorbent structure than the first sensor.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. An absorbent pad for covering a patient support structure, the absorbent pad comprising:
   a periphery having a first portion and a second portion;
   a liquid permeable layer;
   a liquid impermeable base layer;
   an absorbent layer positioned between the liquid permeable layer and the liquid impermeable layer;
   a first sensor positioned between the liquid permeable layer and the liquid impermeable layer, the first sensor indicating when exudate is present at the first sensor; and
   a second sensor positioned between the liquid permeable layer and the liquid impermeable layer, the second sensor indicating when exudate is present at the second sensor;
   wherein the first sensor is positioned in a central portion of the absorbent pad and is not positioned adjacent to the periphery; and
   wherein the second sensor is separated from the first sensor by a first distance, the second sensor is positioned adjacent to the first portion of the periphery and is not positioned adjacent to the second portion of the periphery, and the second sensor indicates that fluid has reached an edge of the patient support structure at the first portion of the periphery.

2. The absorbent pad of claim 1, wherein the first sensor is positioned between the liquid permeable layer and the absorbent layer.

3. The absorbent structure of pad 7, wherein the second sensor is positioned between the absorbent layer and the liquid impermeable layer.

4. The absorbent pad of claim 1, wherein the first sensor is positioned between the absorbent layer and the liquid impermeable layer.

5. The absorbent pad of claim 1, wherein the first sensor is positioned within the absorbent layer.

6. The absorbent pad of claim 5, wherein the second sensor is positioned within the absorbent layer.

7. The absorbent pad of claim 1, wherein the second sensor is positioned between the liquid permeable layer and the absorbent layer.

8. The absorbent pad of claim 1, wherein the first sensor comprises a first RFID tag.

9. The absorbent structure of claim 8, wherein the first RFID tag comprises a tail and an antenna coupled to the tail.

10. The absorbent structure of claim 9, wherein the first RFID tag outputs information indicative an impedance value that varies with an environmental condition in which the antenna and the tail are placed.

11. The absorbent structure of claim 10, wherein the environmental condition is an environmental condition selected from the group consisting of temperature, humidity, wetness, or proximity of an RFID reader to the RFID sensor.

12. The absorbent pad of claim 7, wherein the second sensor comprises a second RFID tag separate from the first RFID tag.

13. The absorbent structure of claim 12, wherein the second RFID tag comprises a second tail and a second antenna coupled to the second tail, and wherein the second RFID tag outputs information indicative an impedance value that varies with an environmental condition in which the second antenna and the second tail are placed.

14. An absorbent pad for covering a patient support structure and for absorbing a liquid emitted by a patient, the absorbent pad having a first area most likely to first be exposed to the liquid, the absorbent structure comprising:
   a periphery having a first portion and a second portion separate and spaced apart from the first portion;
   a liquid permeable layer;
   a liquid impermeable layer;
   an absorbent layer positioned between the liquid permeable layer and the liquid impermeable layer;
   a first interior moisture sensor positioned between the liquid permeable layer and the liquid impermeable layer;
   a first edge moisture sensor positioned between the liquid permeable layer and the liquid impermeable layer; and
   a second edge moisture sensor positioned between the liquid permeable layer and the liquid impermeable layer;
   wherein the first interior moisture sensor is positioned within the absorbent pad first area and the first sensor does not extend outside the first area;
   wherein the first edge sensor is separated and isolated from the first interior sensor by a first distance, the first edge sensor is positioned outside the absorbent pad first area adjacent to the first portion of the periphery, and the first edge sensor indicating when fluid has reached a first edge of the patient support structure within the first portion of the periphery; and
   wherein the second edge sensor is separated and isolated from the first interior sensor by a second distance and from the first edge sensor by a third distance, the second edge sensor is positioned outside the absorbent pad first area adjacent to the second portion of the periphery, and the second edge sensor indicating when fluid has reached a second edge of the patient support structure within the second portion of the periphery.

15. The absorbent pad of claim 14, wherein the second edge sensor is not electrically connected with the first edge sensor.

16. The absorbent pad of claim 14 further comprising a second interior sensor spaced apart from the first interior sensor.

17. The absorbent pad of claim 14, wherein the pad is integrated with a sheet.

18. The absorbent pad of claim 17, wherein the sheet is formed by extending the liquid permeable layer beyond a perimeter of the liquid impermeable layer.

19. The absorbent pad of claim 17, wherein the sheet comprises fitted corners.

20. The absorbent pad of claim 19, wherein the fitted corners are formed by the liquid permeable layer.

* * * * *